(12) United States Patent
Yang

(10) Patent No.: US 6,388,092 B2
(45) Date of Patent: May 14, 2002

(54) HETEROARYL-SUBSTITUTED QUINOLIN-2-ONE DERIVATIVES USEFUL AS ANTICANCER AGENTS

(75) Inventor: Bingwei V. Yang, Waterford, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/836,026

(22) Filed: Apr. 17, 2001

Related U.S. Application Data

(62) Division of application No. 09/501,163, filed on Feb. 9, 2000, now Pat. No. 6,258,824.
(60) Provisional application No. 60/119,702, filed on Feb. 11, 1999.

(51) Int. Cl.[7] .................... C07D 233/02; C07D 233/04; C07D 233/22
(52) U.S. Cl. ................... 548/333.5; 548/311.1; 548/311.4
(58) Field of Search ........... 548/333.5, 311.1, 548/311.4

(56) References Cited

U.S. PATENT DOCUMENTS

| | | | |
|---|---|---|---|
| 4,182,624 A | * | 1/1980 | Soder .................. 71/92 |
| 4,835,154 A | * | 5/1989 | Finkelstein |
| 6,037,350 A | | 3/2000 | Venet et al. |

FOREIGN PATENT DOCUMENTS

| | | |
|---|---|---|
| WO | 9716443 | 5/1997 |
| WO | 9721701 | 6/1997 |
| WO | 9855124 | 12/1998 |

* cited by examiner

*Primary Examiner*—D. Margaret Seaman
(74) *Attorney, Agent, or Firm*—Peter C. Richardson; Paul H. Ginsburg; Adrian G. Looney

(57) ABSTRACT

The present invention relates to compounds of formula 1

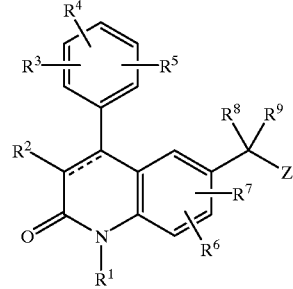

and pharmaceutically acceptable salts and solvates thereof wherein $R^1$, $R^2$, $R^3$, $R^4$, $R^5$, $R^6$, $R^7$, $R^8$, $R^9$, and Z are as defined herein. The invention also relates to pharmaceutical compositions comprising compounds of formula 1 and to methods of inhibiting abnormal cell growth, including cancer, in a mammal by administering compounds of formula 1 to the mammal. The invention also relates to intermediates and methods useful in synthesizing compounds of formula 1.

2 Claims, No Drawings

HETEROARYL-SUBSTITUTED QUINOLIN-2-ONE DERIVATIVES USEFUL AS ANTICANCER AGENTS

This is a division of application Ser. No. 09/501,163 filed Feb. 9, 2000 now U.S. Pat. No. 6,258,824, which claims the benefit of U.S. Provisional Application No. 60/119,702, filed Feb. 11, 1999, both of which are incorporated herein by reference.

BACKGROUND OF THE INVENTION

This invention relates to a series of heteroaryl-substituted quinolin-2-one derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as agents to combat tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993). The compounds of the present invention exhibit activity as inhibitors of the enzyme farnesyl protein transferase and are therefore believed to be useful as anti-cancer and anti-tumor agents. Further, the compounds of the present invention may be active against any tumors that proliferate by virtue of farnesyl protein transferase.

Other compounds that are indicated as having activity inhibiting farnesyl protein transferase are referred to in International Publication Number WO 97/21701, entitled "Farnesyl Protein Transferase Inhibiting (Imidazol-5-yl) methyl-2-quinolinone Derivatives", which has an International Publication Date of Jun. 19, 1997; in International Publication Number WO 97/16443, entitled "Farnesyl Transferase Inhibiting 2-Quinolone Derivatives", which has an International Publication Date of May 9, 1997; PCT/IB99/01393, filed Aug. 5, 1999, entitled "2-Quinolone derivatives Useful as Anticancer Agents"; and PCT/IB99/01398, filed Aug. 6, 1999, entitled "Alkynyl-Substituted Quinolin-2-one Derivatives Useful as Anticancer Agents"; all of which are incorporated herein by reference in their entireties.

The preceding Kohl et al. publication, as well as all other references discussed below in this application, are also hereby incorporated by reference in their entireties.

SUMMARY OF THE INVENTION

The present invention relates to compounds of formula 1

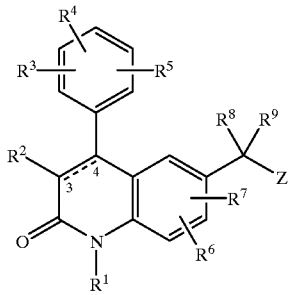

or pharmaceutically acceptable salts or solvates thereof wherein:
the dashed line indicates an optional second bond connecting C-3 and C-4 of the quinolin-2-one ring;
$R^1$ is selected from H, $C_1$–$C_{10}$ alkyl, —$(CR^{13}R^{14})_qC(O)R^{12}$, —$(CR^{13}R^{14})_qC(O)OR^{15}$, —$(CR^{13}R^{14})_qOR^{12}$, —$(CR^{13}R^{14})_qCSO_2R^{15}$, —$(CR^{13}R^{14})_t(C_{3-C10}$ cycloalkyl), —$(CR^{13}R^{14})_t(C_6$–$C_{10}$ aryl), and —$(CR^{13}R^{14})_t(4$–$10$ membered heterocyclic), wherein said cycloalkyl, aryl and heterocyclic $R^1$ groups are optionally fused to a $C_6$–$C_{10}$ aryl group, a $C_5$–$C_8$ saturated cyclic group, or a 4–10 membered heterocyclic group; and the foregoing $R^1$ groups, except H but including any optional fused rings referred to above, are optionally substituted by 1 to 4 $R^6$ groups;
$R^2$ is halo, cyano, —$C(O)OR^{15}$, or a group selected from the substituents provided in the definition of $R^{12}$;
each $R^3$, $R^4$, $R^5$, $R^6$, and $R^7$ is independently selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —$CH=NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t(4$–$10$ membered heterocyclic), —$(CR^{13}R^{14})_t(C_3$–$C_{10}$ cycloalkyl), and —$(CR^{13}R^{14})_tC≡CR^{16}$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t(4$–$10$ membered heterocyclic);
Z is an aromatic 4–10 membered heterocyclic group, substituted by 1 to 4 $R^6$ substituents;
$R^8$ is H, —$OR^{12}$, —$OC(O)R^{12}$, —$NR^{12}R^{13}$, —$N=CR^{12}R^{13}$, —$NR^{12}C(O)R^{13}$, cyano, —$C(O)OR^{13}$, —$SR^{12}$, or —$(CR^{13}R^{14})_t(4$–$10$ membered heterocyclic), wherein said heterocyclic $R^8$ groups are substituted by 1 to 4 $R^6$ groups;
$R^9$ is —$(CR^{13}R^{14})_t(imidazolyl)$ or —$(CR^{13}R^{14})_t(pyridinyl)$ wherein said imidazolyl or pyridinyl moiety is substituted by 1 or 2 $R^6$ substituents each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t$ ($C_6$–$C_{10}$ aryl), and —$(CR^{13}R^{14})_t$(4–10 membered heterocyclic); said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, are optionally substituted by 1 to 3 substituents independently selected from halo, cyano, nitro, trifluoromethyl, trifluoromethoxy, azido, —C(O)$R^{13}$, —C(O)O$R^{13}$, —OC(O)$R^{13}$, —N$R^{13}$C(O)$R^{14}$, —C(O)N$R^{13}R^{14}$, —N$R^{13}R^{14}$, hydroxy, $C_1$–$C_6$ alkyl, and $C_1$–$C_6$ alkoxy;

each t is independently an integer from 0 to 5 and each q is independently an integer from 1 to 5;

each $R^{13}$ and $R^{14}$ is independently H or $C_1$–$C_6$ alkyl, and where $R^{13}$ and $R^{14}$ are as —$(CR^{13}R^{14})_q$ or —$(CR^{13}R^{14})_t$ each is independently defined for each iteration of q or t in excess of 1;

$R^{15}$ is selected from the substituents provided in the definition of $R^{12}$ except $R^{15}$ is not H;

$R^{16}$ is selected from the list of substituents provided in the definition of $R^{12}$ and —Si$R^{17}R^{18}R^{19}$; and, $R^{17}$, $R^{18}$ and $R^{19}$ are each independently selected from the substituents provided in the definition of $R^{12}$ except at least one of $R^{17}$, $R^{18}$ and $R^{19}$ is not H.

Preferred compounds of formula 1 are those wherein Z is a 5 or 6 membered aromatic heterocyclic group substituted with from 1 to 4 $R^6$ substituents. More preferred compounds of formula 1 are those wherein Z is a pyridine or thiophene group substituted with from 1 to 4 $R^6$ substituents. Other preferred compounds of formula 1 are those wherein Z is a 5 or 6 membered aromatic heterocyclic group fused to a benzene group, substituted with from 1 to 4 $R^6$ substituents. Preferably, Z comprises from 1 to 3 heteroatoms selected from O, S and N.

Other preferred compounds of formula 1 are those wherein $R^1$ is H, $C_1$–$C_6$ alkyl, or cyclopropylmethyl.

Other preferred compounds of formula 1 are those wherein $R^8$ is —N$R^{12}R^{13}$, —O$R^{12}$, or —$(CR^{13}R^{14})$t (4–10 membered heterocyclic) substituted with from 1 to 4 $R^6$ groups, wherein said 4–10 membered heterocyclic is selected from triazolyl, imidazolyl, pyrazolyl, and piperidinyl. More preferably, said heterocyclic is substituted with one $R^6$ group. Preferably, $R^8$ is hydroxy, amino, or triazolyl.

Other preferred compound of formula 1 are those wherein $R^8$ is H, —O$R^{12}$, —OC(O)$R^{12}$, —N$R^{12}R^{13}$, —N$R^{12}$C(O)$R^{13}$, cyano, —C(O)O$R^{13}$, —S$R^{12}$, or —$(CR^{13}R^{14})_t$(4–10 membered heterocyclic), wherein said heterocyclic $R^8$ groups are substituted by 1 to 4 $R^6$ groups.

Other preferred compounds of formula 1 are those wherein $R^3$, $R^4$, $R^5$ and $R^6$ are independently selected from H, halo, and $C_1$–$C_6$ alkoxy.

Preferred compounds of the invention include:

6-[amino-(6-chloro-pyridin-3-yl)-(3-methyl-3H-imidazol-4-yl)-methyl]-4-(3-chloro-phenyl)-1-methyl-1H-quinolin-2-one (enantiomer A);

6-[amino-(6-chloro-pyridin-3-yl)-(3-methyl-3H-imidazol-4-yl)-methyl]-4-(3-chloro-phenyl)-1-methyl-1H-quinolin-2-one (enantiomer B);

4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one;

6-[amino-(6-chloro-pyridin-3-yl)-(3-methyl-3H-imidazol-4-yl)-methyl]-4-(3-chloro-phenyl)-1-cyclopropylmethyl-1H-quinolin-2-one;

4-(3-chloro-phenyl)-6-[(5-chloro-pyridin-2-yl)-hydroxy-(3-methyl-3H-imidazol-4-yl)-methyl]-1-methyl-1H-quinolin-2-one;

6-[amino-(5-chloro-pyridin-2-yl)-(3-methyl-3H-imidazol-4-yl)-methyl]-4-(3-chloro-phenyl)-1-methyl-1H-quinolin-2-one;

6-[amino-(5-chloro-pyridin-2-yl)-(3-methyl-3H-imidazol-4-yl)-methyl]-4-(3-chloro-phenyl)-1-cyclopropylmethyl-1H-quinolin-2-one;

6-[amino-(6-chloro-pyridin-3-yl)-(3-methyl-3H-imidazol-4-yl)-methyl]-4-(3,5-dichloro-phenyl)-1-methyl-1H-quinolin-2-one;

6-[amino-(5-chloro-thiophen-2-yl)-(3-methyl-3H-imidazol-4-yl)-methyl]-4-(3-chloro-phenyl)-1-methyl-1H-quinolin-2-one;

6-[(5-chloro-thiophen-2-yl)-hydroxy-(3-methyl-3H-imidazol-4-yl)-methyl]-4-(3-ethoxy-phenyl)-1-methyl-1H-quinolin-2-one;

amino-(5-chloro-thiophen-2-yl)-(3-methyl-3H-imidazol-4-yl)-methyl]-4-(3-ethoxy-phenyl)-1-methyl-1H-quinolin-2-one;

6-[(6-chloro-pyridin-3-yl)-hydroxy-(3-methyl-3H-imidazol-4-yl)-methyl]-4-(3-ethoxy-phenyl)-1-methyl-1H-quinolin-2-one;

6-[amino-(6-chloro-pyridin-3-yl)-(3-methyl-3H-imidazol-4-yl)-methyl]-4-(3-ethoxy-phenyl)-1-methyl-1H-quinolin-2-one;

6-[benzo[b]thiophen-2-yl-hydroxy-(3-methyl-3H-imidazol-4-yl)-methyl]-4-(3-chloro-phenyl)-1-methyl-1H-quinolin-2-one;

6-[amino-(6-chloro-pyridin-3-yl)-(3-methyl-3H-imidazol-4-yl)-methyl]-4-(3-chloro-phenyl)-1H-quinolin-2-one;

(−)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one;

6-[amino-[6-methyl-pyridin-3-yl)-(3-methyl-3H-imidazol-4-yl)-methyl]-(3-chloro-phenyl)-1-methyl-1H-quinolin-2-one;

6-[amino-(pyridin-3-yl)-(3-methyl-3H-imidazol-4-yl)-methyl]-4-(3-chloro-phenyl)-1-cyclopropylmethyl-1H-quinolin-2-one;

(+)-4-(3-chloro-phenyl)-6-[(6-chloro-pyridin-3-yl)-hydroxy-(3-methyl-3H-imidazol-4-methyl]-1-cyclopropylmethyl-1H-quinolin-2-one; and pharmaceutically acceptable salts and solvates of the foregoing compounds.

The present invention also relates to compounds of the formula 12

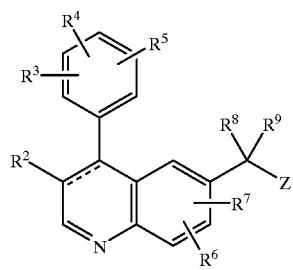

wherein:
the dashed line indicates an optional second bond connecting $C_{-3}$ and $C_{-4}$ of the quinoline ring;

R² is halo, cyano, —C(O)OR¹⁵, or a group selected from the substituents provided in the definition of R¹²;

each R³, R⁴, R⁵, R⁶, and R⁷ is independently selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —OR¹², —C(O)R¹², —C(O)OR¹², —NR¹³C(O)OR¹⁵, —OC(O)R¹², —NR¹³SO₂R¹⁵, —SO₂NR¹²R¹³, —NR¹³C(O)R¹², —C(O)NR¹²R¹³, —NR¹²R¹³, —CH=NOR¹², —S(O)ⱼF¹² wherein j is an integer from 0 to 2, —(CR³¹R¹⁴)ₜ(C₆–C₁₀ aryl), —(CR¹³R¹⁴)ₜ(4–10 membered heterocyclic), —(CR¹³R¹⁴)ₜ(C₃–C₁₀ cycloalkyl), and —(CR¹³R¹⁴)ₜC≡CR¹⁶; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —NR¹³SO₂R¹⁵, —SO₂NR¹²R¹³, —C(O)R¹², —C(O)OR¹², —OC(O)R¹², —NR¹³C(O)OR¹⁵, —NR¹³C(O)R¹², —C(O)NR¹²R¹³, —NR¹²R¹³, —OR¹², $C_1$–$C_{10}$ alkyl, $C_2$–$C_{10}$ alkenyl, $C_2$–$C_{10}$ alkynyl, —(CR¹³R¹⁴)ₜ(C₆–C₁₀ aryl), and —(CR¹³R¹⁴)ₜ(4–10 membered heterocyclic);

Z is an aromatic 4–10 membered heterocyclic group, substituted by 1 to 4 R⁶ substituents;

R⁸ is H, —OR¹², —OC(O)R¹², —NR¹²R¹³, —NR¹²C(O)R¹³, cyano, —C(O)OR¹³, —SR¹², —(CR¹³R¹⁴)ₜ(4–10 membered heterocyclic), wherein said heterocyclic R⁸ groups are substituted by 1 to 4 R⁶ groups;

R⁹ is —(CR¹³R¹⁴)ₜ(imidazolyl) or —(CR¹³R¹⁴)ₜ(pyridinyl) wherein said imidazolyl or pyridinyl moiety is substituted by 1 or 2 R⁶ substituents;

each R¹² is independently selected from H, $C_1$–$C_{10}$ alkyl, —(CR¹³R¹⁴)ₜ(C₃–C₁₀ cycloalkyl), —(CR¹³R¹⁴)ₜ(C₆–C₁₀ aryl), and —(CR¹³R¹⁴)ₜ(4–10 membered heterocyclic); said cycloalkyl, aryl an heterocyclic R¹² groups are optionally fused to a $C_6$–$C_{10}$ aryl group, a $C_5$–$C_8$ saturated cyclic group, or a 4–10 membered heterocyclic group; and the foregoing R¹² substituents, except H but including any optional fused rings, are optionally substituted by 1 to 3 substituents independently selected from halo, cyano, nitro, trifluoromethyl, trifluoromethoxy, azido, —C(O)R¹³, —C(O)OR¹³, —OC(O)R¹³, —NR¹³C(O)R¹⁴, —C(O)NR¹³R¹⁴, —NR¹³R¹⁴, hydroxy, $C_1$–$C_6$ alkyl, and $C_1$–$C_6$ alkoxy;

each t is independently an integer from 0 to 5;

each R¹³ and R¹⁴ is independently H or $C_1$–$C_6$ alkyl, and where R¹³ and R¹⁴ are as —(CR¹³R¹⁴)ₜ each is independently defined for each iteration of t in excess of 1;

R¹⁵ is selected from the substituents provided in the definition of R¹² except R¹⁵ is not H;

R¹⁶ is selected from the list of substituents provided in the definition of R¹² and —SiR¹⁷R¹⁸R¹⁹; and, R¹⁷, R¹⁸ and R¹⁹ are each independently selected from the substituents provided in the definition of R¹² except at least one of R¹⁷, R¹⁸ and R¹⁹ is not H.

Compounds of formula 12 are useful as intermediates for preparing compounds of formula 1. Compounds of formula 12 are also prodrugs of compounds of formula 1, and the present invention also includes pharmaceutically acceptable salts and solvates of compounds of formula 12.

The present invention also relates to compounds of the formula 6

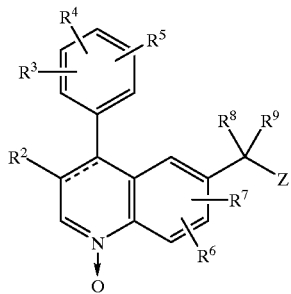

6 wherein:

the dashed line indicates an optional second bond connecting C-3 and C-4 of the quinoline ring;

R² is halo, cyano, —C(O)OR¹⁵, or a group selected from the substituents provided in the definition of R¹²;

each R³, R⁴, R⁵, R⁶, and R⁷ is independently selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —OR¹², —C(O)R¹², —C(O)OR¹², —NR¹³C(O)OR¹⁵, —OC(O)R¹², —NR¹³SO₂R¹⁵, —SO₂NR¹²R¹³, —NR¹³C(O)R¹², —C(O)NR¹²R¹³, —NR¹²R¹³, —CH=NOR¹², —S(O)ⱼR¹² wherein j is an integer from 0 to 2, —(CR¹³R¹⁴)ₜ(C₆–C₁₀ aryl), —(CR¹³R¹⁴)ₜ(4–10 membered heterocyclic), —(CR¹³R¹⁴)ₜ(C₃–C₁₀ cycloalkyl), and —(CR¹³R¹⁴)ₜC≡CR¹⁶; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —NR¹³SO₂R¹⁵, —SO₂NR¹²R¹³, —C(O)R¹², —C(O)OR¹², —OC(O)R¹², —NR¹³C(O)OR¹⁵, —NR¹³C(O)R¹², —C(O)NR¹²R¹³, —NR¹²R¹³, —OR¹², $C_1$–$C_{10}$ alkyl, $C_2$–$C_{10}$ alkenyl, $C_2$–$C_{10}$ alkynyl, —(CR¹³R¹⁴)ₜ(C₆–C₁₀ aryl), and —(CR¹³R¹⁴)ₜ(4–10 membered heterocyclic);

Z is an aromatic 4–10 membered heterocyclic group, substituted by 1 to 4 R⁶ substituents;

R⁸ is H, —OR¹², —OC(O)R¹², —NR¹²R¹³, —NR¹²C(O)R¹³, cyano, —C(O)OR¹³, —SR¹², or —(CR¹³R¹⁴)ₜ(4–10 membered heterocyclic), wherein said heterocyclic R⁸ groups are substituted by 1 to 4 R⁶ groups:

R⁹ is —(CR¹³R¹⁴)ₜ(imidazolyl) or —(CR¹³R¹⁴)ₜ(pyridinyl) wherein said imidazolyl or pyridinyl moiety is substituted by 1 or 2 R⁶ substituents;

each R¹² is independently selected from H, $C_1$–$C_{10}$ alkyl, —(CR¹³R¹⁴)ₜ(C₃–C₁₀ cycloalkyl), —(CR¹³R¹⁴)ₜ(C₆–C₁₀ aryl), and —(CR¹³R¹⁴)ₜ(4–10 membered heterocyclic); said cycloalkyl, aryl a heterocyclic R¹² groups are optionally fused to a $C_6$–$C_{10}$ aryl group, a $C_5$–$C_8$ saturated cyclic group, or a 4–10 membered heterocyclic group; and the foregoing R¹² substituents, except H but including any optional fused rings, are optionally substituted by 1 to 3 substituents independently selected from halo, cyano, nitro, trifluoromethyl, trifluoromethoxy, azido, —C(O)R¹³, —C(O)OR¹³, —OC(O)R¹³, —NR¹³C(O)R¹⁴, —C(O)NR¹³R¹⁴, —NR¹³R¹⁴, hydroxy, $C_1$–$C_6$ alkyl, and $C_1$–$C_6$ alkoxy;

each t is independently an integer from 0 to 5;

each $R^{13}$ and $R^{14}$ is independently H or $C_1$–$C_6$ alkyl, and where $R^{13}$ and $R^{14}$ are as —$(CR^{13}R^{14})_t$ each is independently defined for each iteration of t in excess of 1;

$R^{15}$ is selected from the substituents provided in the definition of $R^{12}$ except $R^{15}$ is not H;

$R^{16}$ is selected from the list of substituents provided in the definition of $R^{12}$ and —$SiR^{17}R^{18}R^{19}$; and, $R^{17}$, $R^{18}$ and $R^{19}$ are each independently selected from the substituents provided in the definition of $R^{12}$ except at least one of $R^{17}$, $R^{18}$ and $R^{19}$ is not H.

Compounds of formula 6 are useful as intermediates for preparing compounds of formula 1. Compounds of formula 6 are furthermore prodrugs of compounds of formula 1, and the present invention also includes pharmaceutically acceptable salts and solvates of compounds of formula 6.

The invention also relates to compounds of the formula 2

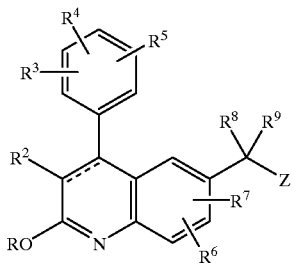

2 wherein:
the dashed line indicates an optional second bond connecting C-3 and C-4 of the quinoline ring;

R is $C_1$–$C_6$ alkyl;

$R^2$ is halo, cyano, —C(O)OR$^{15}$, or a group selected from the substituents provided in the definition of $R^{12}$;

each $R^3$, $R^4$, $R^5$, $R^6$, and $R^7$ is independently selected from H, $C_1$–$C_{10}$ alkyl, $C_2$–$C_{10}$ alkenyl, $C_2$–$C_{10}$alkynyl, halo, cyano, nitro, trifluoromethyl, trifluoromethoxy, azido, —OR$^{12}$, —C(O)R$^{12}$, —C(O)OR$^{12}$, —NR$^{13}$C(O)OR$^{15}$, —OC(O)R$^{12}$, —NR$^{13}$SO$_2$R$^{15}$, —SO$_2$NR$^{12}$R$^{13}$, —NR$^{13}$C(O)R$^{12}$, —C(O)NR$^{12}$R$^{13}$, —NR$^{12}$R$^{13}$, —CH=NOR$^{12}$, —S(O)$_j$R$^{12}$ wherein j is an integer from 0 to 2, —(CR$^{13}$R$^{14}$)$_t$(C$_6$–C$_{10}$ aryl), —(CR$^{13}$R$^{14}$)$_t$(4–10 membered heterocyclic), —(CR$^{13}$R$^{14}$)$_t$(C$_3$–C$_{10}$ cycloalkyl), and —(CR$^{13}$R$^{14}$)$_t$C≡CR$^{16}$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —NR$^{13}$SO$_2$R$^{15}$, —SO$_2$NR$^{12}$R$^{13}$, —C(O)R$^{12}$, —C(O)OR$^{12}$, —OC(O)R$^{12}$, —NR$^{13}$C(O)OR$^{15}$, —NR$^{13}$C(O)R$^{12}$, —C(O)NR$^{12}$R$^{13}$, —NR$^{12}$R$^{13}$, —OR$^{12}$, $C_1$–$C_{10}$ alkyl, $C_2$–$C_{10}$ alkenyl, $C_2$–$C_{10}$ alkynyl, —(CR$^{13}$R$^{14}$)$_t$(C$_6$–C$_{10}$ aryl), and —(CR$^{13}$R$^{14}$)$_t$(4–10 membered heterocyclic);

Z is an aromatic 4–10 membered heterocyclic group, substituted by 1 to 4 $R^6$ substituents;

$R^8$ is H, —OR$^{12}$, —OC(O)R$^{12}$, —NR$^{12}$R$^{13}$, —NR$^{12}$C(O)R$^{13}$, cyano, —C(O)OR$^{13}$, —SR$^{12}$, or —(CR$^{13}$R$^{14}$)$_t$(4–10 membered heterocyclic), wherein said heterocyclic $R^8$ groups are substituted by 1 to 4 $R^6$ groups;

$R^9$ is —(CR$^{13}$R$^{14}$)$_t$(imidazolyl) or —(CR$^{13}$R$^{14}$)$_t$(pyridinyl) wherein said imidazolyl or pyridinyl moiety is substituted by 1 or 2 $R^6$ substituents;

each $R^{12}$ is independently selected from H, $C_1$–$C_{10}$ alkyl, —(CR$^{13}$R$^{14}$)$_t$ ($C_3$–$C_{10}$ cycloalkyl), —(CR$^{13}$R$^{14}$)$_t$ ($C_6$–$C_{10}$ aryl), and —(CR$^{13}$R$^{14}$)$_t$(4–10 membered heterocyclic); said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, are optionally substituted by 1 to 3 substituents independently selected from halo, cyano, nitro, trifluoromethyl, trifluoromethoxy, azido, —C(O)R$^{13}$, —C(O)OR$^{13}$, —OC(O)R$^{13}$, —NR$^{13}$C(O)R$^{14}$, —C(O)NR$^{13}$R$^{14}$, —NR$^{13}$R$^{14}$, hydroxy, $C_1$–$C_6$ alkyl, and $C_1$–$C_6$ alkoxy;

each t is independently an integer from 0 to 5;

each $R^{13}$ and $R^{14}$ is independently H or $C_1$–$C_6$ alkyl, and where $R^{13}$ and $R^{14}$ are as —(CR$^{13}$R$^{14}$)$_t$ each is independently defined for each iteration of t in excess of 1;

$R^{15}$ is selected from the substituents provided in the definition of $R^{12}$ except $R^{15}$ is not H;

$R^{16}$ is selected from the list of substituents provided in the definition of $R^{12}$ and —SiR$^{17}$R$^{18}$R$^{19}$; and, $R^{17}$, $R^{18}$ and $R^{19}$ are each independently selected from the substituents provided in the definition of $R^{12}$ except at least one of $R^{17}$, $R^{18}$ and $R^{19}$ is not H. Compounds of formula 2 are useful as intermediates for preparing compounds of formula 1. Compounds of formula 2 are furthermore prodrugs of compounds of formula 1, and the present invention also includes pharmaceutically acceptable salts and solvates of compounds of formula 2.

This invention also relates to a method of inhibiting abnormal cell growth in a mammal, including a human, comprising administering to said mammal an amount of a compound of the formula 1, 2, 12, or 6, as defined above, or a pharmaceutically acceptable salt or solvate thereof, that is effective in inhibiting farnesyl protein transferase.

This invention also relates to a method of inhibiting abnormal cell growth in a mammal, including a human, comprising administering to said mammal an amount of a compound of the formula 1, 2, 12, or 6 as defined above, or a pharmaceutically acceptable salt or solvate thereof, that is effective in inhibiting abnormal cell growth.

The invention also relates to a method for the inhibition of abnormal cell growth in a mammal which comprises administering to said mammal a therapeutically effective amount of a compound of formula 1, 2, 12, or 6, or a pharmaceutically acceptable salt or solvate thereof, in combination with a chemotherapeutic. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention further relates to a method for inhibiting abnormal cell growth in a mammal which method comprises administering to the mammal an amount of a compound of formula 1, 2, 12, or 6, or a pharmaceutically acceptable salt or solvate thereof, in combination with radiation therapy, wherein the amount of the compound, salt, ot solvate of formula 1, 2, 12, or 6 is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula 1, 2, 12, or 6 can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula 1, 2, 12, or 6, or a pharmaceutically acceptable salt or solvate thereof, which amount is effective in sensitizing abnormal cells to treatment with radiation. The amount of the compound, salt, or solvate in this method can be determined according to the means for ascertaining effective amounts of such compounds described herein.

This invention also relates to a pharmaceutical composition for inhibiting abnormal cell growth in a mammal, including a human, comprising an amount of a compound of the formula 1, 2, 12, or 6 as defined above, or a pharmaceutically acceptable salt or solvate thereof, that is effective in inhibiting farnesyl protein transferase, and a pharmaceutically acceptable carrier.

This invention also relates to a pharmaceutical composition for inhibiting abnormal cell growth in a mammal, including a human, comprising an amount of a compound of the formula 1, 2, 12, or 6 as defined above, or a pharmaceutically acceptable salt or solvate thereof, that is effective in inhibiting abnormal cell growth, and a pharmaceutically acceptable carrier.

The invention also relates to a pharmaceutical composition for the inhibition of abnormal cell growth in a mammal which comprises a therapeutically effective amount of a compound of formula 1, 2, 12, or 6 or a pharmaceutically acceptable salt or solvate thereof, in combination with a chemotherapeutic, and a pharmaceutically acceptable carrier. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of and a pharmaceutical composition for treating in a mammal a disease or condition selected from lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system, (e.g., primary CNS lymphoma, spinal axis tumors, brain stem gliomas or pituitary adenomas), Barrett's esophagus (pre-malignant syndrome), neoplastic cutaneous disease, psoriasis, mycoses fungoides, benign prostaric hypertrophy, human papilloma virus (HPV), and restinosis which comprise an amount of a compound of formula 1, 2, 12, or 6, or a pharmaceutically acceptable salt or solvate of such a compound, that is effective in inhibiting farnesyl protein transferase.

The invention also relates to a method of and pharmaceutical composition for treating in a mammal a disease or condition selected from lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem gliomas or pituitary adenomas), Barrett's esophagus (pre-malignant syndrome), neoplastic cutaneous disease, psoriasis, mycoses fungoides, benign prostatic hypertrophy, human papilloma virus (HPV), and restinosis which comprise an amount of a compound of formula 1, 2, 12, or 6, or a pharmaceutically acceptable salt or solvate of such a compound, that is effective in treating said disease.

This invention also relates to a method of and to a pharmaceutical composition for inhibiting abnormal cell growth in a mammal which comprise an amount of a compound of formula 1, 2, 12, or 6, or a pharmaceutically acceptable salt or solvate thereof, and an amount of one or more substances selected from anti-angiogenesis agents, signal transduction inhibitors, and antiproliferative agents, which amounts are together effective in inhibiting abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1, 2, 12, or 6, in the methods and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S.

Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

- 3-[[4-(4-fluoro-phenoxy)benzenesulfonyl]-(1-hydroxycarbamoyl-cyclopentyl)-amino]-propionic acid;
- 3-exo-3-[4-(4-fluoro-phenoxy)-benzenesulfonylamino]-8-oxa-bicyclo[3.2.1]octane-3-carboxylic acid hydroxamide;
- (2R,3R) 1-[4-(2-chloro-4-fluoro-benzyloxy)-benzenesulfonyl]-3-hydroxy-3-methyl-piperidine-2-carboxylic acid hydroxyamide;
- 4-[4-(4-fluoro-phenoxy)-benzenesulfonylamino]-tetrahydro-pyran-4-carboxylic acid hydroxyamide;
- 3-[[4-(4-fluoro-phenoxy)-benzenesulfonyl]-(1-hydroxycarbamoyl-cyclobutyl)-amino]-propionic acid;
- 4-[4-(4-chloro-phenoxy)-benzenesulfonylamino]-tetrahydro-pyran-4-carboxylic acid hydroxyamide;
- (R) 3-[4-(4-chloro-phenoxy)-benzenesulfonylamino]-tetrehydro-pyran-3-carboxylic acid hydroxyamide;
- (2R,3R) 1-[4-(4-fluoro-2-methyl-benzyloxy)-benzenesulfonyl]-3-hydroxy-3-methyl-piperidine-2-carboxylic acid hydroxyamide;
- 3-[[4-(4-fluoro-phenoxy)-benzenesulfonyl]-(1-hydroxycarbamoyl-1-methyl-ethyl)-amino]-propionic acid;
- 3-[[4-(4-fluoro-phenoxy)-benzenesulfonyl]-(4-hydroxycarbamoyl-tetrahydro-pyran-4-yl)-amino]-propionic acid;
- 3-exo-3-[4-(4-chloro-phenoxy)benzenesulfonylamino]-8-oxa-bicyclo[3.2.1]octane-3-carboxylic acid hydroxyamide;
- 3-endo-3-[4-(4-fluoro-phenoxy)-benzenesulfonylamino]-8-oxa-bicyclo[3.2.1]octane-3-carboxylic acid hydroxyamide; and
- (R) 3-[4-(4-fluoro-phenoxy)benzenesulfonylamino]-tetrahydro-furan-3-carboxylic acid hydroxyamide;

and pharmaceutically acceptable salts and solvates of said compounds.

Other anti-angiogenesis agents, including other COX-II inhibitors and other MMP inhibitors, can also be used in the present invention.

A compound of formula 1, 2, 12, or 6, can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with a compound of formula 1, 2, 12, or 6. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome pic), and the monoclonal antibodies AR-209 (Aronex Pharmaceuticals Inc. of The Woodlands, Tex., USA) and 2B-1 (Chiron), can furthermore be combined with a compound of formula 1, 2, 12, or 6, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with a compound of formula 1, 2, 12, or 6, in accordance with the present invention.

A compound of formula 1, 2, 12, or 6, can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application No. 60/113,647 (filed Dec. 23, 1998) which is incorporated by reference in its entirety, however other CTLA4 antibodies can be used in the present invention.

The invention also relates to compounds of the formula 13

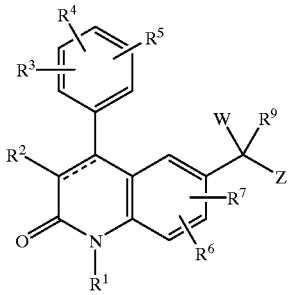

13 wherein:
the dashed line indicates an optional second bond connecting C-3 and C-4 of the quinolin-2-one ring;
W is selected from fluoro, chloro, bromo, and iodo;
$R^1$ is selected from H, $C_1$–$C_{10}$ alkyl, —$(CR^{13}R^{14})_qC(O)R^{12}$, —$(OR^{13}R^{14})_qC(O)OR^{15}$, —$(CR^{13}R^{14})_qOR^{12}$, —$(CR^{13}R^{14})_qCSO_2R^{15}$, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t$(4–10 membered heterocyclic), wherein said cycloalkyl, aryl and heterocyclic $R^1$ groups are optionally fused to a $C_6$–$C_{10}$ aryl group, a $C_5$–$C_8$ saturated cyclic group, or a 4–10 membered heterocyclic group; and the foregoing $R^1$ groups, except H but including any optional fused rings referred to above, are optionally substituted by 1 to 4 $R^6$ groups;
$R^2$ is halo, cyano, —$C(O)OR^{15}$, or a group selected from the substituents provided in the definition of $R^{12}$;
each $R^3$, $R^4$, $R^5$, $R^6$, and $R^7$ is independently selected from H, $C_1$–$C_{10}$ alkyl, $C_2$–$C_{10}$ alkenyl, $C_2$–$C_{10}$alkynyl, halo, cyano, nitro, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —$CH=NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14})_t(C_3$–$C_{10}$ cycloalkyl), and —$(CR^{13}R^{14})_tC\equiv CR^{16}$; and wherein the cycloalkyl, aryl and heterocyclic moieties of the foregoing groups are optionally fused to a $C_6$–$C_{10}$ aryl group, a $C_6$–$C_{10}$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t$(4–10 membered heterocyclic);
Z is an aromatic 4–10 membered heterocyclic group, substituted by 1 to 4 $R^6$ substituents;

$R^9$ is —$(CR^{13}R^{14})_t$(imidazolyl) or —$(CR^{13}R^{14})_t$(pyridinyl) wherein said imidazolyl or pyridinyl moiety is substituted by 1 or 2 $R^6$ substituents;
each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t$(4–10 membered heterocyclic); said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;
each t is independently an integer from 0 to 5 and each q is independently an integer from 1 to 5;
each $R^{13}$ and $R^{14}$ is independently H or $C_1$–$C_6$ alkyl, and where $R^{13}$ and $R^{14}$ are as —$(CR^{13}R^{14})_q$ or —$(CR^{13}R^{14})_t$ each is independently defined for each iteration of q or t in excess of 1;
$R^{15}$ is selected from the substituents provided in the definition of $R^{12}$ except $R^{15}$ is not H;
$R^{16}$ is selected from the list of substituents provided in the definition of $R^{12}$ and —$SiR^{17}R^{18}R^{19}$; and,
$R^{17}$, $R^{18}$ and $R^{19}$ are each independently selected from the substituents provided in the definition of $R^{12}$ except at least one of $R^{17}$, $R^{18}$ and $R^{19}$ is not H. Compounds of formula 13 are useful as intermediates for preparing compounds of formula 1.

The invention also relates to compounds of the formula 29

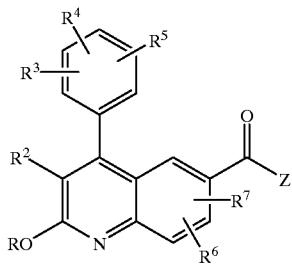

29 wherein:
R is $C_1$–$C_6$ alkyl;
$R^2$ is halo, cyano, —$C(O)OR^{15}$, or a group selected from the substituents provided in the definition of $R^{12}$;
each $R^3$, $R^4$, $R^5$, $R^6$, and $R^7$ is independently selected from H, $C_1$–$C_{10}$ alkyl, $C_2$–$C_{10}$ alkenyl, $C_2$–$C_{10}$alkynyl, halo, cyano, nitro, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —$CH=NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14})_t(C_3$–$C_{10}$ cycloalkyl), and —$(CR^{13}R^{14})_tC\equiv CR^{16}$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —NR$^{13}$SO$_2$R$^{15}$, —SO$_2$NR$^{12}$R$^{13}$, —C(O)R$^{12}$, —C(O)OR$^{12}$, —OC(O)R$^{12}$, —NR$^{13}$C(O)OR$^{15}$, —NR$^{13}$C(O)R$^{12}$, —C(O)NR$^{12}$R$^{13}$, —NR$^{12}$R$^{13}$, —OR$^{12}$, C$_1$–C$_{10}$ alkyl, C$_2$–C$_{10}$ alkenyl, C$_2$–C$_{10}$ alkynyl, —(CR$^{13}$R$^{14}$)$_t$(C$_6$–C$_{10}$ aryl), and —(CR$^{13}$R$^{14}$)$_t$(4–10 membered heterocyclic);

Z is an aromatic 4–10 membered heterocyclic group, substituted by 1 to 4 R$^6$ substituents;

each R$^{12}$ is independently selected from H, C$_1$–C$_{10}$ alkyl, —(CR$^{13}$R$^{14}$)$_t$(C$_3$–C$_{10}$ cycloalkyl) —(CR$^{13}$R$^{14}$)$_t$(C$_6$–C$_{10}$ aryl), and —(CR$^{13}$R$^{14}$)$_t$(4–10 membered heterocyclic); said cycloalkyl, aryl and heterocyclic R$^{12}$ groups are optionally fused to a C$_6$–C$_{10}$ aryl group, a C$_5$–C$_8$ saturated cyclic group, or a 4–10 membered heterocyclic group; and the foregoing R$^{12}$ substituents, except H but including any optional fused rings, are optionally substituted by 1 to 3 substituents independently selected from halo, cyano, nitro, trifluoromethyl, trifluoromethoxy, azido, —C(O)R$^{13}$, —C(O)OR$^{13}$, —OC(O)R$^{13}$, —NR$^{13}$C(O)R$^{14}$, —C(O)NR$^{13}$R$^{14}$, —NR$^{13}$R$^{14}$, hydroxy, C$_1$–C$_6$ alkyl, and C$_1$–C$_6$ alkoxy;

each t is independently an integer from 0 to 5;

each R$^{13}$ and R$^{14}$ is independently H or C$_1$–C$_6$ alkyl, and where R$^{13}$ and R$^{14}$ are as —(CR$^{13}$R$^{14}$)$_t$ each is independently defined for each iteration t in excess of 1;

R$^{15}$ is selected from the substituents provided in the definition of R$^{12}$ except R$^{15}$ is not H;

R$^{16}$ is selected from the list of substituents provided in the definition of R$^{12}$ and —SiR$^{17}$R$^{18}$R$^{19}$; and, R$^{17}$, R$^{18}$ and R$^{19}$ are each independently selected from the substituents provided in the definition of R$^{12}$ except at least one of R$^{17}$, R$^{18}$ and R$^{19}$ is not H. Compounds of formula 29 are useful as intermediates for preparing compounds of formula 1.

The invention also relates to compounds of the formula 30

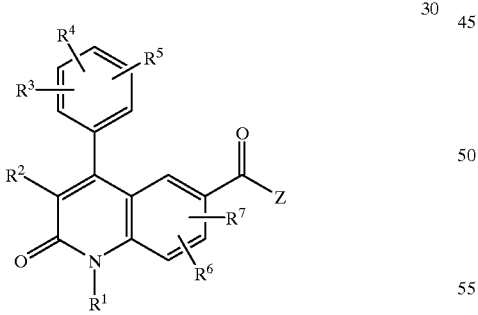

30 wherein:

R$^1$ is selected from H, C$_1$–C$_{10}$ alkyl, —(CR$^{13}$R$^{14}$)$_q$C(O)R$^{12}$, —(CR$^{13}$R$^{14}$)$_q$C(O)OR$^{15}$, —(CR$^{13}$R$^{14}$)$_q$OR$^{12}$, —(CR$^{13}$R$^{14}$)$_q$CSO$_2$R$^{15}$, —(CR$^{13}$R$^{14}$)$_t$(C$_3$–C$_{10}$ cycloalkyl), —(CR$^{13}$R$^{14}$)$_t$(C$_6$–C$_{10}$ aryl), and —(CR$^{13}$R$^{14}$)$_t$(4–10 membered heterocyclic), wherein said cycloalkyl, aryl and heterocyclic R$^1$ groups are optionally fused to a C$_6$–C$_{10}$ aryl group, a C$_5$–C$_8$ saturated cyclic group, or a 4–10 membered heterocyclic group; and the foregoing R$^1$ groups, except H but including any optional fused rings referred to above, are optionally substituted by 1 to 4 R$^6$ groups;

R$^2$ is halo, cyano, —C(O)OR$^{15}$, or a group selected from the substituents provided in the definition of R$^{12}$;

each R$^3$, R$^4$, R$^5$, R$^6$, and R$^7$ is independently selected from H, C$_1$–C$_{10}$ alkyl, C$_2$–C$_{10}$ alkenyl, C$_2$–C$_{10}$alkynyl, halo, cyano, nitro, trifluoromethyl, trifluoromethoxy, azido, —OR$^{12}$, —C(O)R$^{12}$, —C(O)OR$^{12}$, —NR$^{13}$C(O)OR$^{15}$, —OC(O)R$^{12}$, —NR$^{13}$SO$_2$R$^{15}$, —SO$_2$NR$^{12}$R$^{13}$, —NR$^{13}$C(O)R$^{12}$, —C(O)NR$^{12}$R$^{13}$, —NR$^{12}$R$^{13}$, —CH=NOR$^{12}$, —S(O)$_j$R$^{12}$ wherein j is an integer from 0 to 2, —(CR$^{13}$R$^{14}$)$_t$(C$_6$–C$_{10}$ aryl), —(CR$^{13}$R$^{14}$)$_t$(4–10 membered heterocyclic), —(CR$^{13}$R$^{14}$)$_t$(C$_3$–C$_{10}$ cycloalkyl), and —(CR$^{13}$R$^{14}$)$_t$C≡CR$^{16}$; and wherein the cycloalkyl, aryl and heterocyclic moieties of the foregoing groups are optionally fused to a C$_6$–C$_{10}$ aryl group, a C$_5$–C$_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —NR$^{13}$SO$_2$R$^{15}$, —SO$_2$NR$^{12}$R$^{13}$, —C(O)R$^{12}$, —C(O)OR$^{12}$, —OC(O)R$^{12}$, —NR$^{13}$C(O)OR$^{15}$, —NR$^{13}$C(O)R$^{12}$, —C(O)NR$^{12}$R$^{13}$, —NR$^{12}$R$^{13}$, —OR$^{12}$, C$_1$–C$_{10}$ alkyl, C$_2$–C$_{10}$ alkenyl, C$_2$–C$_{10}$ alkynyl, —(CR$^{13}$R$^{14}$)$_t$(C$_6$–C$_{10}$ aryl), and —(CR$^{13}$R$^{14}$)$_t$(4–10 membered heterocyclic);

Z is an aromatic 4–10 membered heterocyclic group, substituted by 1 to 4 R$^6$ substituents;

each R$^{12}$ is independently selected from H, C$_1$–C$_{10}$ alkyl, —(CR$^{13}$R$^{14}$)$_t$(C$_3$–C$_{10}$ cycloalkyl), —(CR$^{13}$R$^{14}$)$_t$(C$_6$–C$_{10}$ aryl), and —(CR$^{13}$R$^{14}$)$_t$(4–10 membered heterocyclic); said cycloalkyl, aryl and heterocyclic R$^{12}$ groups are optionally fused to a C$_6$–C$_{10}$ aryl group, a C$_5$–C$_8$ saturated cyclic group, or a 4–10 membered heterocyclic group; and the foregoing R$^{12}$ substituents, except H but including any optional fused rings, are optionally substituted by 1 to 3 substituents independently selected from halo, cyano, nitro, trifluoromethyl, trifluoromethoxy, azido, —C(O)R$^{13}$, —C(O)OR$^{13}$, —OC(O)R$^{13}$, —NR$^{13}$C(O)R$^{14}$, —C(O)NR$^{13}$R$^{14}$, —NR$^{13}$R$^{14}$, hydroxy, C$_1$–C$_6$ alkyl, and C$_1$–C$_6$ alkoxy;

each t is independently an integer from 0 to 5 and each q is independently an integer from 1 to 5;

each R$^{13}$ and R$^{14}$ is independently H or C$_1$–C$_6$ alkyl, and where R$^{13}$ and R$^{14}$ are as —(CR$^{13}$R$^{14}$)$_q$ or —(CR$^{13}$R$^{14}$)$_t$ each is independently defined for each iteration of q or t in excess of 1;

R$^{15}$ is selected from the substituents provided in the definition of R$^{12}$ except R$^{15}$ is not H;

R$^{16}$ is selected from the list of substituents provided in the definition of R$^{12}$ and —SiR$^{17}$R$^{18}$R$^{19}$; and, R$^{17}$, R$^{18}$ and R$^{19}$ are each independently selected from the substituents provided in the definition of R$^{12}$ except at least one of R$^{17}$, R$^{18}$ and R$^{19}$ is not H. Compounds of formula 30 are useful as intermediates for preparing compounds of formula 1.

The invention also relates to compounds of the formula 26

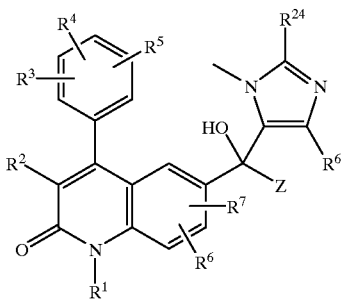

26 wherein:
- $R^{24}$ is selected from —$SR^{20}$ and —$SiR^{21}R^{22}R^{23}$, wherein $R^{20}$ is selected from H and phenyl, and $R^{21}$, $R^{22}$, and $R^{23}$ are independently selected from $C_1$–$C_6$ alkyl and phenyl;
- $R^1$ is selected from H, $C_1$–$C_{10}$ alkyl, —$(CR^{13}R^{14})_qC(O)$ $R^{12}$, —$(CR^{13}R^{14})_qC(O)OR^{15}$, —$(CR^{13}R^{14})_qOR^{12}$, —$(CR^{13}R^{14})_qCSO_2R^{15}$, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t$(4–10 membered heterocyclic), wherein said cycloalkyl, aryl and heterocyclic $R^1$ groups are optionally fused to a $C_6$–$C_{10}$ aryl group, a $C_5$–$C_8$ saturated cyclic group, or a 4–10 membered heterocyclic group; and the foregoing $R^1$ groups, except H but including any optional fused rings referred to above, are optionally substituted by 1 to 4 $R^6$ groups;
- $R^2$ is halo, cyano, —$C(O)OR^{15}$, or a group selected from the substituents provided in the definition of $R^{12}$;
  - each $R^3$, $R^4$, $R^5$, $R^6$, and $R^7$ is independently selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —$CH=NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14})_t(C_3$–$C_{10}$ cycloalkyl), and —$(CR^{13}R^{14})_tC≡CR^{16}$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^3C(O)$ $R^{12}$, —$C(O)NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t$ $(C_6$–$C_{10}$ aryl), and —$(CR^{13}R^{14})_t$(4–10 membered heterocyclic);
- Z is an aromatic 4–10 membered heterocyclic group, substituted by 1 to 4 $R^6$ substituents;
- each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t$ $(C_6$–$C_{10}$ aryl), and —$(CR^{13}R^{14})_t$(4–10 membered heterocyclic); said cycloalkyl, aryl a heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;
- each t is independently an integer from 0 to 5 and each q is independently an integer from 1 to 5;
- each $R^{13}$ and $R^{14}$ is independently H or $C_1$–$C_6$ alkyl, and where $R^{13}$ and $R^{14}$ are as —$(CR^{13}R^{14})_q$ or —$(CR^{13}R^{14})_t$ each is independently defined for each iteration of q or t in excess of 1;
- $R^{15}$ is selected from the substituents provided in the definition of $R^{12}$ except $R^{15}$ is not H;
- $R^{16}$ is selected from the list of substituents provided in the definition of $R^{12}$ and —$SiR^{17}R^{18}R^{19}$; and,
- $R^{17}$, $R^{18}$ and $R^{19}$ are each independently selected from the substituents provided in the definition of $R^{12}$ except at least one of $R^{17}$, $R^{18}$ and $R^{19}$ is not H. Compounds of formula 26 are useful as intermediates for preparing compounds of formula 1.

The invention also relates to a method of synthesizing a compound of the formula

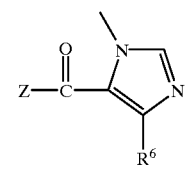

11a wherein
- $R^6$ is selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —$OR^{12}$, —$C(O)R^{12}$, —$C(O)$ $OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —$C=NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14})_t(C_3$–$C_{10}$ cycloalkyl), and —$(CR^{13}R^{14})_tC≡CR^{16}$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)$ $R^{12}$, —$NR^{13}C(O)OR^{15}$, —$NR^{13}C(O)R^{12}$, —$C(O)$ $NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t$(4–10 membered heterocyclic);
- Z is an aromatic 4–10 membered heterocyclic group, substituted by 1 to 4 $R^6$ substituents;
- each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t$ $(C_6$–$C_{10}$ aryl), and —$(CR^{13}R^{14})_t$(4–10 membered heterocyclic); said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, ere optionally substituted by 1 to 3 substituents independently selected from halo, cyano, nitro, trifluoromethyl, trifluoromethoxy, azido, —C(O)R$^{13}$, —C(O)OR$^{13}$, —OC(O)R$^{13}$, —NR$^{13}$C(O)R$^{14}$, —C(O)NR$^{13}$R$^{14}$, —NR$^{13}$R$^{14}$, hydroxy, C$_1$–C$_6$ alkyl, and C$_1$–C$_6$ alkoxy;

each t is independently an integer from 0 to 5;

each R$^{13}$ and R$^{14}$ is independently H or C$_1$–C$_6$ alkyl, and where R$^{13}$ and R$^{14}$ are as —(CR$^{13}$R$^{14}$)$_t$ each is independently defined for each iteration of t in excess of 1;

R$^{15}$ is selected from the substituents provided in the definition of R$^{12}$ except R$^{15}$ is not H;

R$^{16}$ is selected from the list of substituents provided in the definition of R$^{12}$ and —SiR$^{17}$R$^{18}$R$^{19}$; and, R$^{17}$, R$^{18}$ and R$^{19}$ are each independently selected from the substituents provided in the definition of R$^{12}$ except at least one of R$^{17}$, R$^{18}$ and R$^{19}$ is not H;

which method comprises reacting in an appropriate solvent in the presence of a suitable base a compound of the formula

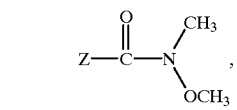

28 wherein Z is as defined above;

with a compound of the formula

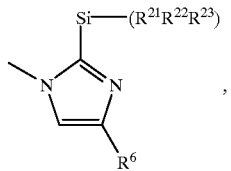

33 wherein R$^6$ is as defined above, and

R$^{21}$, R$^{22}$, and R$^{23}$ are each independently selected from C$_1$–C$_6$ alkyl and phenyl; thereby obtaining a compound of the formula

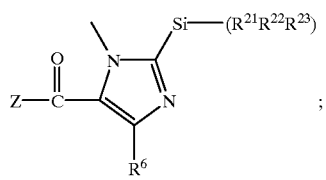

32 and reacting the compound of formula 32 so obtained in an appropriate solvent with acetic acid or with a fluoride reagent. Said method can be used in preparing compounds of formula 1.

The invention also relates to a method of synthesizing a compound of the formula

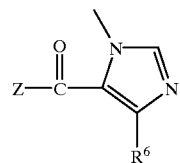

11a wherein

R$^1$ is selected from H, C$_1$–C$_{10}$ alkyl, C$_2$–C$_{10}$ alkenyl, C$_2$–C$_{10}$ alkynyl, halo, cyano, nitro, trifluoromethyl, trifluoromethoxy, azido, —OR$^{12}$, —C(O)R$^{12}$, —C(O)OR$^{12}$, —NR$^{13}$C(O)OR$^{15}$, —OC(O)R$^{12}$, —NR$^{13}$SO$_2$R$^{15}$, —SO$_2$NR$^{12}$R$^{13}$, —NR$^{13}$C(O)R$^{12}$, —C(O)NR$^{12}$R$^{13}$, —NR$^{12}$R$^{13}$, —CH=NOR$^{12}$, —S(O)$_j$R$^{12}$ wherein j is an integer from 0 to 2, —(CR$^{13}$R$^{14}$)$_t$(C$_6$–C$_{10}$ aryl), —(CR$^{13}$R$^{14}$)$_t$(4–10 membered heterocyclic), —(CR$^{13}$R$^{14}$)$_t$(C$_3$–C$_{10}$ cycloalkyl), and —(CR$^{13}$R$^{14}$)$_t$C≡R$^{16}$; and wherein the cycloalkyl, aryl and heterocyclic moieties of the foregoing groups are optionally fused to a C$_6$–C$_{10}$ aryl group, a C$_5$–C$_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —NR$^{13}$SO$_2$R$^{15}$, —SO$_2$NR$^{12}$R$^{13}$, —C(O)R$^{12}$, —C(O)OR$^{12}$, —OC(O)R$^{12}$, —NR$^{13}$C(O)OR$^{15}$, —NR$^{13}$C(O)R$^{12}$, —C(O)NR$^{12}$R$^{13}$, —NR$^{12}$R$^{13}$, —OR$^{12}$, C$_1$–C$_{10}$ alkyl, C$_2$–C$_{10}$ alkenyl, C$_2$–C$_{10}$ alkynyl, —(CR$^{13}$R$^{14}$)$_t$(C$_6$–C$_{10}$ aryl), and —(CR$^{13}$R$^{14}$)$_t$(4–10 membered heterocyclic);

Z is an aromatic 4–10 membered heterocyclic group, substituted by 1 to 4 R$^6$ substituents;

each R$^{12}$ is independently selected from H, C$_1$–C$_{10}$ alkyl, —(CR$^{13}$R$^{14}$)$_t$(C$_3$–C$_{10}$ cycloalkyl), —(CR$^{13}$R$^{14}$)$_t$(C$_6$–C$_{10}$ aryl), and —(CR$^{13}$R$^{14}$)$_t$(4–10 membered heterocyclic); said cycloalkyl, aryl and heterocyclic R$^{12}$ groups are optionally fused to a C$_6$–C$_{10}$ aryl group, a C$_5$–C$_8$ saturated cyclic group, or a 4–10 membered heterocyclic group; and the foregoing R$^{12}$ substituents, except H but including any optional fused rings, are optionally substituted by 1 to 3 substituents independently selected from halo, cyano, nitro, trifluoromethyl, trifluoromethoxy, azido, —C(O)R$^{13}$, —C(O)OR$^{13}$, —OC(O)R$^{13}$, —NR$^{13}$C(O)R$^{14}$, —C(O)NR$^{13}$R$^{14}$, —NR$^{13}$R$^{14}$, hydroxy, C$_1$–C$_6$ alkyl, and C$_1$–C$_6$ alkoxy;

each t is independently an integer from 0 to 5;

each R$^{13}$ and R$^{14}$ is independently H or C$_1$–C$_6$ alkyl, and where R$^{13}$ and R$^{14}$ are as —(CR$^{13}$R$^{14}$)$_t$ each is independently defined for each iteration of t in excess of 1;

R$^{15}$ is selected from the substituents provided in the definition of R$^{12}$ except R$^{15}$ is not H;

R$^{16}$ is selected from the list of substituents provided in the definition of R$^{12}$ and —SiR$^{17}$R$^{18}$R$^{19}$; and, R$^{17}$, R$^{18}$ and R$^{19}$ are each independently selected from the substituents provided in the definition of R$^{12}$ except at least one of R$^{17}$, R$^{18}$ and R$^{19}$ is not H;

which method comprises reacting in an appropriate solvent in the presence of a suitable base a compound of the formula

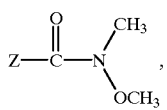

wherein Z is as defined above;
with a compound of the formula

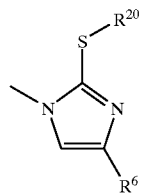

wherein $R^6$ is as defined above and $R^{20}$ is selected from H and phenyl;
thereby obtaining a compound of the formula

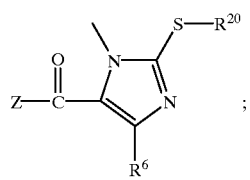

and removing from the compound of formula 31 so obtained the —$SR^{20}$ group, either:
a) reductively, with a nickel catalyst; or
b) oxidatively, with nitric acid or with aqueous hydrogen peroxide in acetic acid. Said method can be used in preparing compounds of formula 1.

The invention also relates to a method of synthesizing a compound of the formula

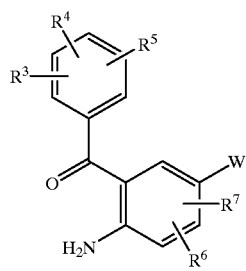

wherein
each $R^3$, $R^4$, $R^5$, $R^6$, and $R^7$ is independently selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —$OR^{12}$, —$C(O)R^{12}$, —$C(O)OR^{12}$, —NR C(O) $OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —CH=$NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14})_t$ $(C_3$–$C_{10}$ cycloalkyl), and —$(CR^{13}R^{14})_tC$≡$CR^{16}$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t$(4–10 membered heterocyclic);

each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t$ $(C_6$–$C_{10}$ aryl), and —$(CR^{13}R^{14})_t$(4–10 membered heterocyclic); said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;

each t is independently an integer from 0 to 5;
each $R^{13}$ and $R^{14}$ is independently H or $C_1$–$C_6$ alkyl, and where $R^{13}$ and $R^{14}$ are as —$(CR^{13}R^{14})_t$ each is independently defined for each iteration of t in excess of 1;
$R^{15}$ is selected from the substituents provided in the definition of $R^{12}$ except $R^{15}$ is not H;
$R^{16}$ is selected from the list of substituents provided in the definition of $R^{12}$ and —$SiR^{17}R^{18}R^{19}$; and,
$R^{17}$, $R^{18}$ and $R^{19}$ are each independently selected from the substituents provided in the definition of $R^{12}$ except at least one of $R^{17}$, $R^{18}$ and $R^{19}$ is not H;
which method comprises reacting, at a temperature of from about −78° C. to about 0° C., in the presence of a suitable base and in an appropriate solvent a compound of formula

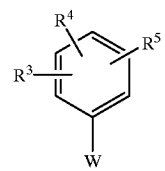

wherein W is an appropriate leaving group, and $R^3$, $R^4$ and $R^5$ are as defined above,
with a compound of the formula

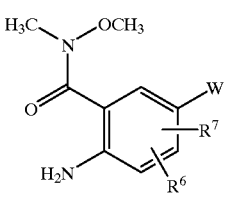

wherein $R^6$ and $R^7$ are as defined above. Said method can be used in preparing compounds of formula 1. In a preferred embodiment of the above-described method for synthesizing a compound of formula 23, the solvent in which the compound of formula 34 and the compound of formula 35 are reacted is ethyl ether.

The invention also pertains to a method of synthesizing a compound of the formula

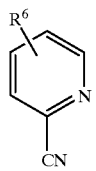

37 wherein $R^6$ is selected from H, $C_1$–$C_{10}$ alkyl, $C_2$–$C_{10}$ alkenyl, $C_2$–$C_{10}$alkynyl, halo, cyano, nitro, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^3C(O)R^2$, —$C(O)NR^{12}R^{13}$, —$NR^{12}$, —$NR^{12}R^{13}$, —CH=$NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14})_t(C_3$–$C_{10}$ cycloalkyl), and —$(CR^{13}R^{14})_tC{\equiv}CR^{16}$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t$(4–10 membered heterocyclic);

which method comprises a) reacting with a metal cyanide, in the presence of a palladium catalyst and in an appropriate solvent, at a temperature of about 25° C. to about 100° C., a compound of the formula

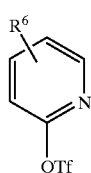

36 wherein Tf is —$SO_2$—$CF_3$ and $R^6$ is as defined above; thereby obtaining a compound of the formula 37. This method is useful in the preparation of compounds of formula 1.

In one embodiment of the method described in the immediately preceding paragraph, a compound of the formula

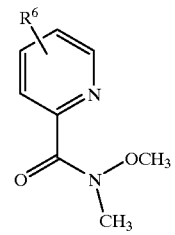

28a is further synthesized, wherein $R^6$ is selected from H, $C_1$–$C_{10}$ alkyl, $C_2$–$C_{10}$ alkenyl, $C_2$–$C_{10}$alkynyl, halo, cyano, nitro, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —CH=$NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14})_t(C_6$–$C_{10}$ cycloalkyl), and —$(CR^{13}R^{14})_tC{\equiv}CR^6$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$NR^{12}R^{13}$, —$OR^{12}$, $C_1$–$C_{10}$ alkyl, $C_2$–$C_{10}$ alkenyl, $C_2$–$C_{10}$ alkynyl, —$(CR^{13}R^{14})_t(C_6$–$C_{10}$ aryl), and —$(CR^{13}R^{14})_t$(4–10 membered heterocyclic);

each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t$(4–10 membered heterocyclic); said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;

each t is independently an integer from 0 to 5;

each $R^{13}$ and $R^{14}$ is independently H or $C_1$–$C_6$ alkyl, and where $R^{13}$ and $R^{14}$ are as —$(CR^{13}R^{14})_t$ each is independently defined for each iteration of t in excess of 1;

$R^{15}$ is selected from the substituents provided in the definition of $R^{12}$ except $R^{15}$ is not H;

$R^{16}$ is selected from the list of substituents provided in the definition of $R^{12}$ and —$SiR^{17}R^{18}R^{19}$; and, $R^{17}$, $R^{18}$ and $R^{19}$ are each independently selected from the substituents provided in the definition of $R^{12}$ except at least one of $R^{17}$, $R^{18}$ and $R^{19}$ is not H;

which embodiment comprises a) reacting with a metal cyanide, in the presence of a palladium catalyst and in an appropriate solvent, at a temperature of about 25° C. to about 100° C., a compound of the formula

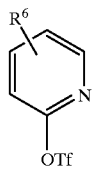

wherein Tf is —SO$_2$—CF$_3$ and R$^6$ is as defined above;
thereby obtaining a compound of the formula

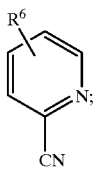

b) treating the compound of formula 37 so obtained with either a suitable base or a suitable acid under hydrolysis conditions;
thereby obtaining a compound of the formula

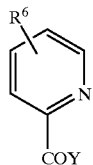

wherein Y is OH;
c) converting the compound of formula 38 so obtained to a compound of the formula

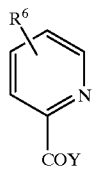

wherein Y is —Cl or N1-imidazole; and
d) treating the compound of formula 38 obtained in (c) with N,O-dimethylhydroxyamine, in the presence of a suitable base and in an appropriate solvent, at a temperature of from about 0° C. to about 40° C. Said embodiment can also be used in preparing compounds of formula 1.

"Abnormal cell growth", as used herein, refers to cell growth that is independent of normal regulatory mechanisms (e.g., loss of contact inhibition). This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma vinus (HPV), and restinosis. "Abnormal cell growth" also refers to and includes the abnormal growth of cells, both benign and malignant, resulting from activity of the enzyme farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties. Examples of allyl groups include, but are not limited to, methyl, ethyl, propyl, isopropyl, and t-butyl.

The term "cycloalkyl", as used herein, unless otherwise indicated, includes cyclic alkyl moieties wherein alkyl is as defined above. Multicyclic, such as bicyclic and tricyclic, groups are included in this definition.

The term "alkenyl", as used herein, unless otherwise indicated, includes alkyl moieties having at least one carbon—carbon double bond wherein alkyl is as defined above.

The term "alkynyl", as used herein, unless otherwise indicated, includes alkyl moieties having at least one carbon—carbon triple bond wherein alkyl is as defined above. Examples of alkynyl groups include, but are no limited to, ethynyl and 2-propynyl.

The term "alkoxy", as used herein, unless otherwise indicated, includes O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "heterocyclic", as used herein, unless otherwise indicated, means aromatic and non-aromatic heterocyclic groups (including saturated heterocyclic groups) containing one or more heteroatoms each selected from O, S and N, wherein each ring of a heterocyclic group has from 4 to 10 atoms. Non-aromatic heterocyclic groups may include rings having only 4 atoms, but aromatic heterocyclic rings must have at least 5 atoms. Heterocyclic groups of this invention unless otherwise indicated may contain one ring or more than one ring, i.e. they may be monocyclic or multicyclic, for example bicyclic (which may comprise non-aromatic and/or aromatic rings). Preferably, bicyclic heterocyclic groups of this invention contain 6–9 members in their ring systems. Monocyclic heterocyclic groups of this invention preferably contain 5 or 6 members. Aromatic multicyclic heterocyclic groups include benzofused ring systems. The heterocyclic groups of this invention can also include ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, piperidinyl, 1,2,3,6-tetrahydropyridinyl, pyrrolinyl, indolinyl, 2H-pyranyl, 4H-pyranyl, dioxanyl, 1,3- dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

Where $R^{13}$ and $R^{14}$ are as $(CR^{13}R^{14})_q$ or $(CR^{13}R^{14})_t$, each $R^{13}$ and $R^{14}$ is independently defined for each iteration of q or t in excess of 1. This means, for instance, that where q or t is 2 alkylene moieties of the type —CH$_2$CH(CH$_3$)—, and other asymmetrically branched groups, are included.

The term "pharmaceutically acceptable salt(s)", as used herein, unless otherwise indicated, includes salts of acidic or basic groups that may be present in the compounds of formula 1. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

Certain compounds of formula 1 may have asymmetric centers and therefore exist in different enantiomeric forms. All optical isomers and stereoisomers of the compounds of formula 1, and mixtures thereof, are considered to be within the scope of the invention. With respect to the compounds of formula 1, the invention includes the use of a racemate, one or more enantiomeric forms, one or more diastereomeric forms, or mixtures thereof. The compounds of formula 1 may also exist as tautomers. This invention relates to the use of all such tautomers and mixtures thereof.

The subject invention also includes prodrugs of compounds of formula 1, which prodrugs are derivatives of compounds of formula 1, which compounds comprise free amino groups, said derivatives comprising amide, carbamide, or peptide derivations of said amino groups. Such prodrugs can comprise an amino acid residue, or a polypeptide chain of two or more, such as up to four, amino acid residues, that are covalently joined through peptide bonds. Amino acid residues useful in preparing prodrugs of the invention include the 20 naturally-occurring amino acids designated by three letter symbols, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Preferred amino acid residues are those with a nonpolar group such as Ala, Val, Nval, Leu, Met, Gly, Pro, Phe, or a basic polar group such as Lys.

The subject invention also includes prodrugs of compounds of formula 1, which prodrugs are the compounds of formula 2, formula 12 and the compounds of formula 6 described herein.

The subject invention also includes isotopically-labelled compounds, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{33}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples below, by substituting a readily available isotopically labelled reagent for a non-isotopically labelled reagent.

Patients that can be treated with a compound of formula 1, 2, 6, or 12, or a pharmaceutically acceptable salt or solvate thereof, according to the methods of this invention include, for example, patients that have been diagnosed as having lung cancer, NSCLC (non small cell lung cancer), bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, brain stem gliomas or pituitary adenomas), neoplastic cutaneous diseases (e.g. psoriasis, mycoses fungoides), or Barrett's esophagus (pre-malignant syndrome).

The compounds of formula 1, 2, 12, and 6, and their pharmaceutically acceptable salts and solvates can each independently also furthermore be used in a palliative neoadjuvant/adjuvant therapy in alleviating the symptoms associated with the diseases recited in the preceding paragaph as well as the symptoms associated with abnormal cell growth. Such therapy can be a monotherapy or can be in a combination with chemotherapy and/or immunotherapy.

Patients that can be treated according to the methods of this invention also include patients suffering from abnormal cell growth, as defined above.

DETAILED DESCRIPTION OF THE INVENTION

In the following Schemes and Examples, "Et" represents an ethyl moiety, and "Me" represents a methyl moiety.

Hence, for example, "OEt" means ethanol. Also, "THF" means tetrahydrofuran, and "DMF" means dimethylformamide.

The compounds of formula 1 may be prepared as described below.

With reference to Scheme 1 below, the compounds of formula 1 may be prepared by hydrolysing an intermediate ether of formula 2, wherein R is $C_1$–$C_6$ alkyl, according to methods familiar to those skilled in the art, such as by stirring the intermediate of formula 2 in an aqueous acid solution. An appropriate acid is, for example, hydrochloric acid. The resulting quinolinone of formula 1 wherein $R^1$ is hydrogen may be transformed into a quinolinone wherein $R_1$ has a meaning as defined above apart from hydrogen by N-alkylation methods familiar to those skilled in the art.

Scheme 1

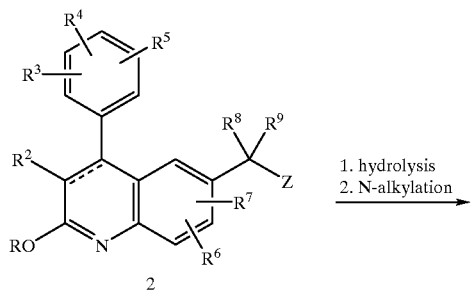

With reference to Scheme 2 below, the intermediate of formula 2, referred to above, may be prepared by reacting an intermediate of formula 10, wherein W is an appropriate leaving group, such as halo, with an intermediate ketone of formula 11. This reaction is done by converting the intermediate of formula 10 into a organometallic compound, by stirring it with a strong base such as butyl lithium, and subsequently adding the intermediate ketone of formula 11. Although this reaction gives at first instance a hydroxy derivative ($R^8$ is hydroxy), said hydroxy derivative can be converted into other intermediates wherein $R^8$ has another definition by performing functional group transformations familiar to those skilled in the art.

Scheme 2

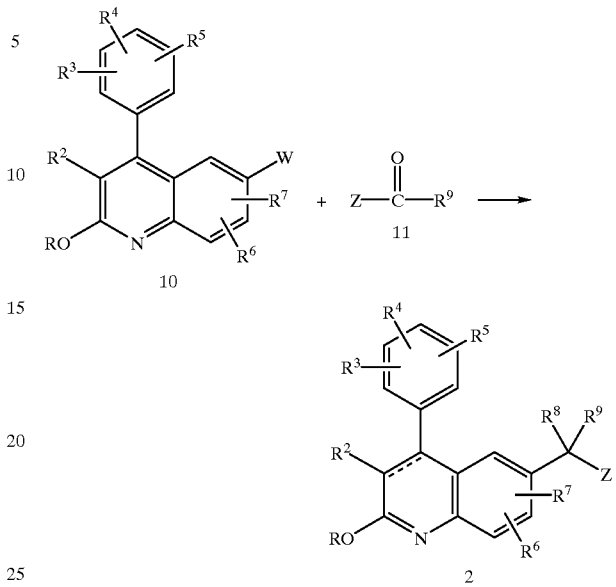

With reference to Scheme 3 below, compounds of formula 36, which are compounds of formula 1 wherein the dotted line is a bond and $R^1$ is hydrogen, can be prepared via ring opening of the isoxazole moiety of the intermediate of formula 22 by stirring it with an acid, such as $TiCl_3$, in the presence of water. Subsequent treatment of the resulting intermediate of formula 23 with a suitable reagent, such as $R^2CH_2COCl$ or $R^2CH_2COOC_2H_5$, wherein R is as defined above, yields either directly a compound of formula 36 or an intermediate which can be converted to a compound of formula 36 by treatment with a base, such as potassium tert-butoxide. The intermediate of formula 36 can be converted to intermediate of formula 10 by stirring it with an o-alkylation reagent, such as trimethyloxonium tetrafluoroborate ($BF_4OMe_3$) for a period of time, typically 4 to 15 hours, and subsequently adding a strong base such as sodium hydroxide in aqueous.

Scheme 3

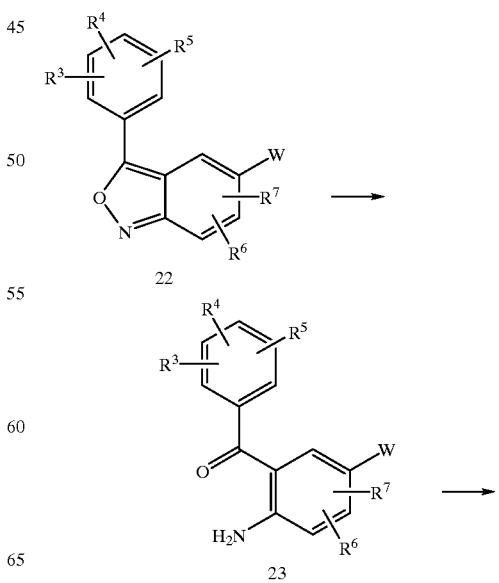

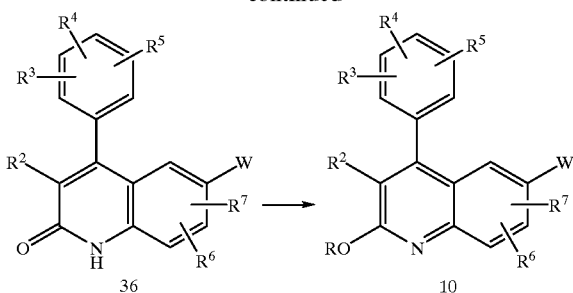

With reference to Scheme 4 below, compounds of formula 1 wherein $R^8$ is a radical of formula $-NR^{12}R^{13}$ wherein $R^{12}$ and $R^{13}$ are as described above (said compounds are represented below by formula 1(g)), may be prepared by reacting an intermediate of formula 13, wherein W is an appropriate leaving group, such as halo, with a reagent of formula 14. Said reaction may be performed by stirring the reactants in an appropriate solvent, such as THF.

Scheme 4

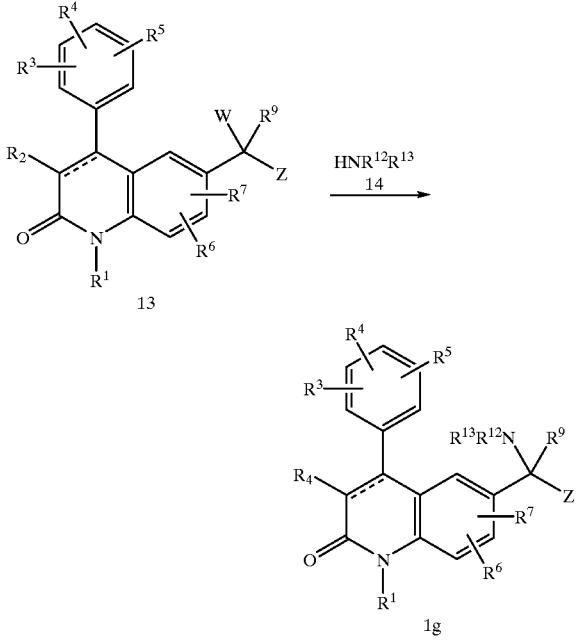

Compounds of formula 1(g), or other embodiments of formula 1, wherein the dotted line represents a bond can be converted into compounds wherein the dotted line does not represent a bond by hydrogenation methods familiar to those skilled in the art. Compounds wherein the dotted line does not represent a bond may be converted into compounds wherein the dotted line represents a bond by oxidation methods familiar to those skilled in the art.

With reference to Scheme 5 below, compounds of formula 1 wherein $R^8$ is hydroxy (said compounds being represented by formula 1(b)) may be converted into compounds of formula 1(c), wherein $R^{12}$ has the meaning described above except it is not hydrogen, by methods known to those skilled in the art, including C-alkylation or O-acylation reactions; such as by reacting the compound of formula 1(b) with an alkylating reagent such as $R^{12}$—W, wherein $R^{12}$ is as described above, in appropriate conditions, such as in a dipolar aprotic solvent, such as DMF, in the presence of a base, such as sodium hydride. W is a suitable leaving group, such as a halo group or a sulfonyl group.

Scheme 5

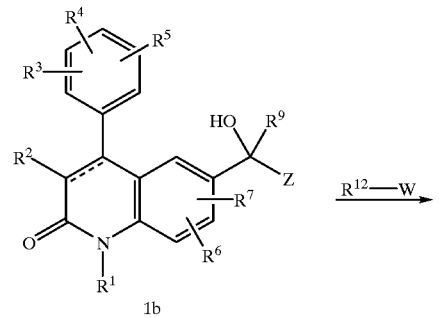

As an alternative to the above reaction procedure, compounds of formula 1(c) may also be prepared by reacting a compound of formula 1(b) with a reagent of formula $R^{12}$—OH, wherein $R^{12}$ is as described above, in acidic medium.

Compounds of formula 1(b) may also be converted into compounds of formula 1(g), wherein $R^{12}$ is hydrogen and $R^{13}$ is replaced with $C_1$–$C_6$ alkylcarbonyl, by reacting compounds of formula 1(b) in acidic medium, such as sulfuric acid, with $C_1$–$C_6$ alkyl-CN in a Rifler-type reaction. Further, compounds of formula 1(b) may also be converted into compounds of formula 1 (g), wherein $R^{12}$ and $R^{13}$ are hydrogen, by reacting a compound of formula 1(b) with ammonium acetate and subsequent treatment with $NH_3$(aq.).

With reference to Scheme 6 below, compounds of formula 1(b), referred to above, may also be converted into compounds of formula 1(d), wherein $R^8$ is hydrogen, by submitting a compound of formula 1(b) to appropriate reducing conditions, such as stirring in trifluoroacetic acid in the presence of an appropriate reducing agent, such as sodium borohydride, or, alternatively, stirring the compound of formula 1(b) in acetic acid in the presence of formamide. Further, the compound of formula 1(d) wherein $R^8$ is hydrogen may be converted into a compound of formula 1(e) wherein $R^{12}$ is $C_1$–$C_{10}$ alkyl by reacting the compound of formula 1(d) with a reagent of formula 5, wherein W is an appropriate leaving group, in an appropriate solvent, such as diglyme, in the presence of a base, such as potassium tert-butoxide.

Scheme 6

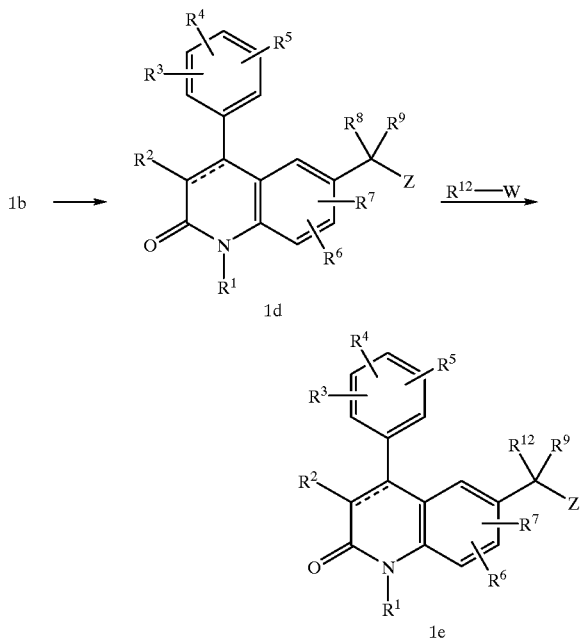

With reference to Scheme 7 below, compounds of formula 1 may be prepared by reacting a nitrone of formula 6 with the anhydride of a carboxylic acid, such as acetic anhydride, thus forming the corresponding ester on the 2-position of the quinoline moiety. Said quinoline ester can be hydrolyzed in situ to the corresponding quinolinone using a base, such as potassium carbonate.

Scheme 7

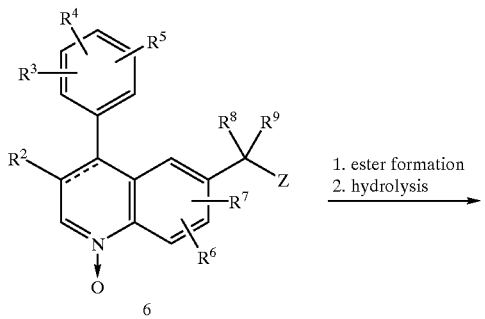

Alternatively, compounds of formula 1 can be prepared by reacting a nitrone of formula 6 with a sulfonyl containing electrophilic reagent, such as p-toluenesulfonylchloride, in the presence of a base, such as aqueous potassium carbonate. The reaction initially involves the formation of a 2-hydroxyquinoline derivative which is subsequently tautomerized to the desired quinolinone derivative. The application of conditions of phase transfer catalysis, which are familiar to those skilled in the art, may enhance the rate of the reaction.

Compounds of formula 1 may also be prepared by an intramolecular photochemical rearrangement of compounds of formula 6, referred to above. Said rearrangement can be carried out by dissolving the reagents in a reaction-inert solvent and irradiating at a wavelength of 366 nm. It is advantageous to use degassed solutions and to conduct the reaction under an inert atmosphere, such as oxygen-free argon or nitrogen gas, in order to minimize undesired side reactions or reduction of quantum yield.

The substituents of the compounds of formula 1 may be converted to other substituents falling within the scope of formula 1 via reactions or functional group transformations familiar to those skilled in the art. A number of such transformations are already described above. Other examples are hydrolysis of carboxylic esters to the corresponding carboxylic acid or alcohol; hydrolysis of amides to the corresponding carboxylic acids or amines; hydrolysis of nitrites to the corresponding amides; amino groups on imidazole or phenyl moieties may be replaced by hydrogen by diazotation reactions familiar to those skilled in the art, and subsequent replacement of the diazo-group by hydrogen; alcohols may be converted into esters and ethers; primary amines may be converted into secondary or tertiary amines; double bonds may be hydrogenated to the corresponding single bond.

With reference to Scheme 8 below, intermediates of formula 29, wherein R is, as defined above, $C_1$–$C_6$ alkyl, may be prepared by reacting an intermediate of formula 10 with an intermediate of formula 28, or a functional derivative thereof, under appropriate conditions. This reaction is done by converting the intermediate of formula 10 into an organometallic compound, by stirring it with a strong base such as butyl lithium, and subsequently adding the intermediate amide of formula 28.

Scheme 8

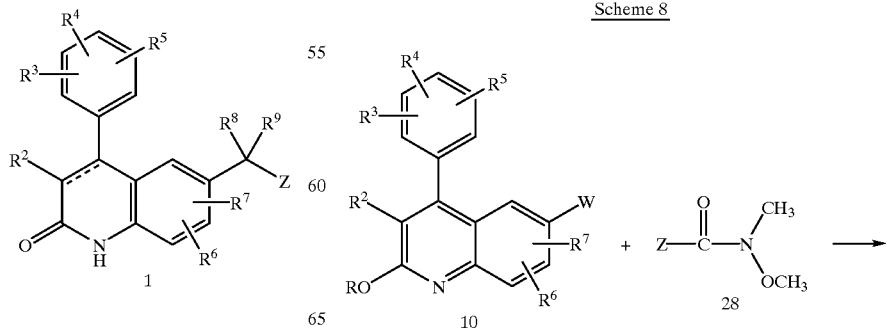

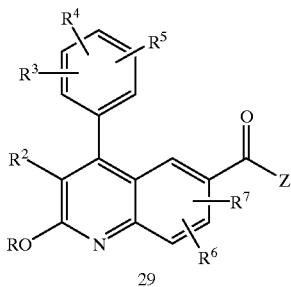

29

With reference to Scheme 9 below, the intermediate nitrones of formula 6 can be prepared by N-oxidizing a quinoline derivative of formula 12 with an appropriate oxidizing agent, such as m-chloro-peroxybenzoic acid or $H_2O_2$, in an appropriate solvent, such as dichloromethane.

Said N-oxidation may also be carried out on a precursor of a quinoline of formula 12.

The intermediate of formula 12 may be metabolized in vivo into compounds of formula 1 via intermediates of formula 6. Hence, intermediates of formula 12 and 6 can act as prodrugs of compounds of formula 1. Also, the intermediates of formula 2 can be metabolized in vivo to compounds of formula 1. Hence, compounds of formula 2 are deemed "prodrugs" for purposes of the present invention. Such prodrugs are within the scope of the present invention.

Scheme 9

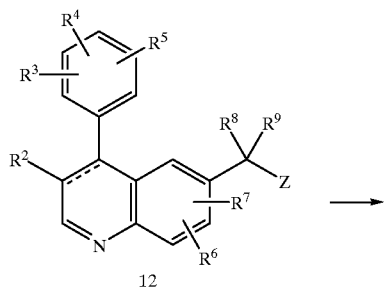

With reference to Scheme 10 below, the compound of formula 30 can be prepared by hydrolysing an intermediate formula 29, wherein R is $C_1$–$C_6$ alkyl, according to methods familiar to those skilled in the art, such as by stirring the intermediate of formula 29 in an aqueous acid solution or in an organic solvent with the presence of a Lewis acid. An appropriate acid is, for example, hydrochloric acid. An appropriate Lewis acid and the solvent are, for example, iodotrimethylsilane and dicholoromethane. The resulting quinolinone of formula 30 wherein $R^1$ is hydrogen may be transformed into a quinolinone wherein $R^1$ has a meaning as defined above apart from hydrogen by N-alkylation methods familiar to those skilled in the art.

Scheme 10

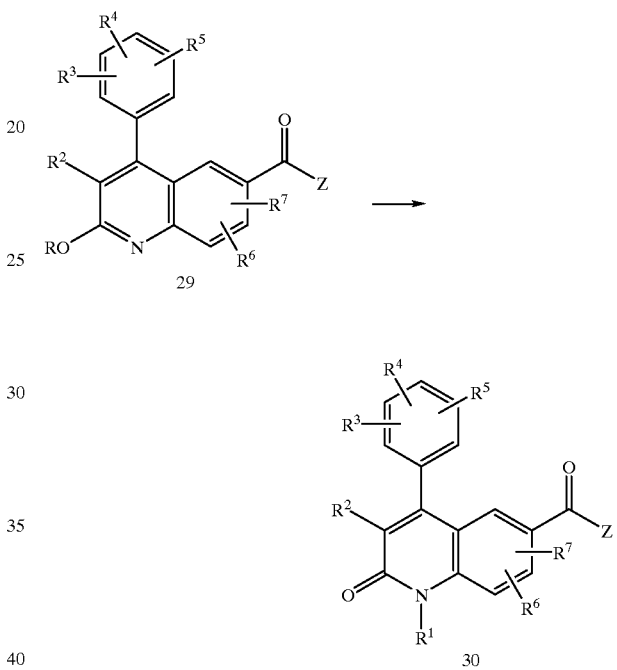

With reference to Scheme 11 below, the compound of formula 26 can be prepared by reacting a compound of formula 30 with an intermediate of formula 27, where $R^{24}$ is $SR^{25}$ or $SiR^{21}R^{22}R^{23}$, $R^{20}$ being H or phenyl, and $R^{21}$, $R^{22}$, and $R^{23}$ being independently selected from $C_1$–$C_6$ alkyl and phenyl. This reaction requires the presence of a suitable base, such as tert-butyl lithium (when $R^{24}$ is $SR^{20}$ and $R^{20}$=H) or lithium 2,2,6,6,-tetramethylpiperidine (when $R^{24}$ is $SR^{20}$ and $R^{20}$=phenyl), or n-butyl lithium (when $R^{24}$ is $SiR^{21}R^{22}R^{23}$), in an appropriate solvent, such as THF. The —$SR^{20}$ group can be reductively removed from the compound of formula 26 with a nickel catalyst such as RANEY™ nickel or oxidatively with nitric acid or aqueous hydrogen peroxide in acetic acid. When $R^{24}$ is $SiR^{21}R^{22}R^{23}$, then $R^{24}$ can be removed from the compound of formula 26 by reaction with acetic acid or a fluoride reagent such as tetrabutylammonia fluoride (TBAF) in a solvent such as tetrahydrofuran. Thus, a compound of formula 1 can be synthesized.

Scheme 11

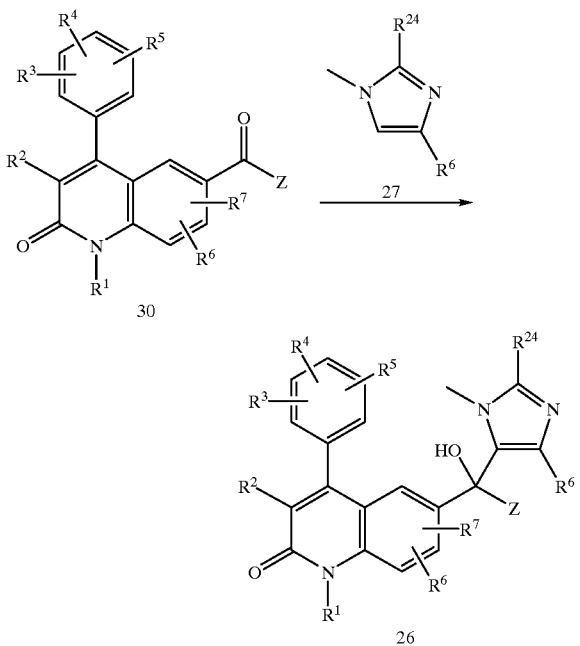

With reference to Scheme 12, intermediates of formula 11a, which are compounds of formula 11 wherein $R^9$ is imidazole substituted with $R^6$, wherein $R^6$ is as defined above, can be prepared by reacting an intermediate of formula 28 with an intermediate of formula 27 where $R^{21}, R^{22}, R^{33}$ are $C_1-C_6$ alkyl or phenyl to generate an intermediate of formula 32. This reaction requires the presence of a suitable base, such as n-butyl lithium, in an appropriate solvent, such as THF. The intermediate of formula 32 is reacted with acetic acid or a fluoride reagent such as TBAF in a solvent such as tetrahydrofuran to obtain the compound of formula 11a. Alternatively, the compound of formula 11a can be prepared by reacting a compound of formula 28 with an intermediate of formula 27 where $R^{20}$ is H or phenyl. This reaction requires the presence of a suitable base, such as tert-butyl lithium (when $R^{20}$=H) or lithium 2,2,6,6,-tetramethylpiperidine (when $R^{20}$=phenyl), in an appropriate solvent, such as THF. The —$SR^{20}$ group can be reductively removed from the compound of formula 31 with a nickel catalyst such as RANEY™ nickel or oxidatively with nitric acid or aqueous hydrogen peroxide in acetic acid.

Scheme 12

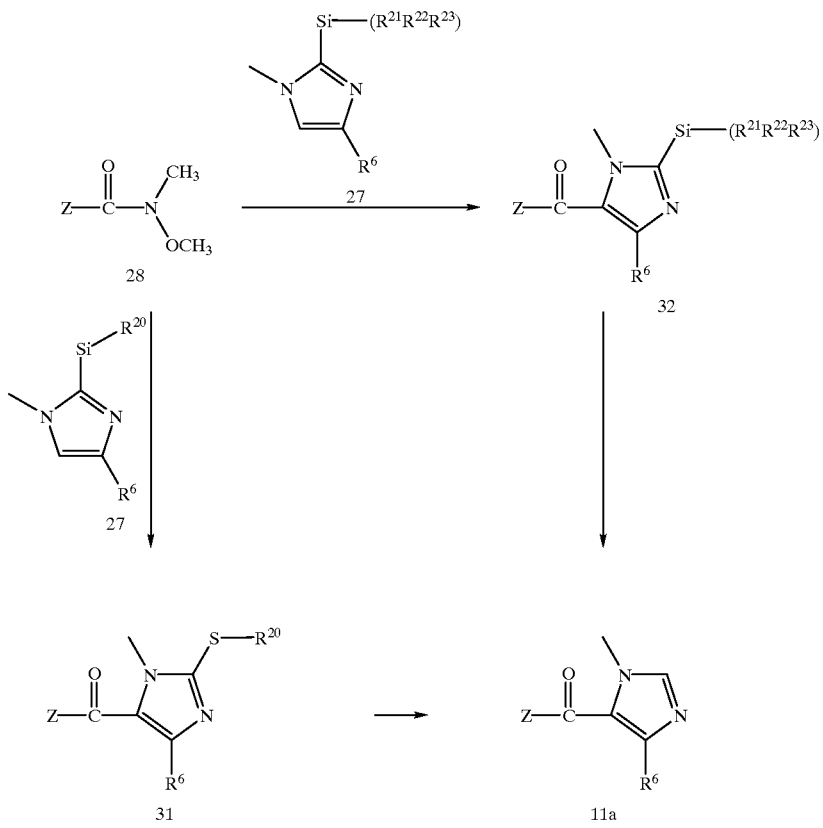

With reference to Scheme 13, intermediates of formula 23 may also be synthesized by reacting an intermediate of formula 34, wherein W is an appropriate leaving group, such as halo, with an intermediate amide of formula 35. This reaction requires the presence of a suitable base, such as n-butyl lithium, in an appropriate solvent, such as diethyl ether at a temperature of from about −78 to about zero degrees C.

Scheme 13

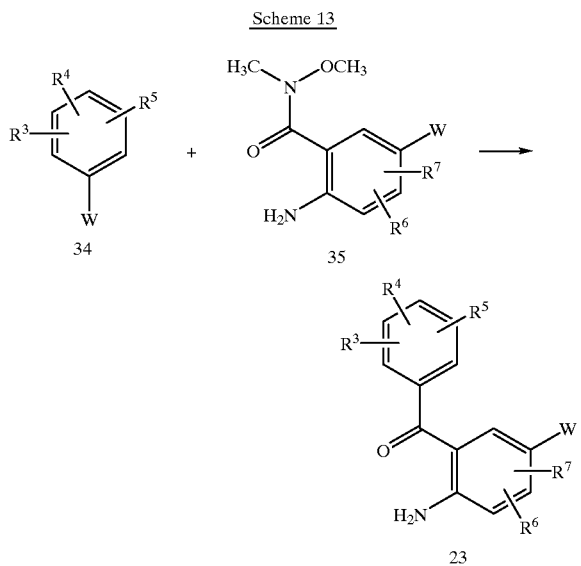

With reference to Scheme 14, intermediates of formula 28a, which are compounds of formula 28 wherein Z is a pyridine substituted with $R^6$, can be prepared by reacting an intermediate of formula 36 with a metal cyanide, such as $Zn(CN)_2$ or NaCN, in the presence of a palladium catalyst such as tetrakis(triphenylphosphine)-palladium, in an appropriate solvent, such as THF or DMF, at a temperature of from about 25 to about 100 degrees C. Subsequent treatment of the resulting intermediate of formula 37 with either a base or acid under hydrolysis conditions familiar to those skilled in the art, yields a compound of formula 38a which are compounds of formula 38 wherein Y is —OH. The intermediate of formula 38 can be converted to its activated form, intermediate 38b which are compounds of formula 38 wherein Y is —Cl or N1-imidazole using methods familiar to those skilled in the art. Subsequent conversion to 28a is furnished with N,O-dimethylhydroxyamine in the presence of a base, such as triethylamine, pyridine, or 4-dimethyaminopyridine, in an appropriate solvent, such as dichloromethane at a temperature of from about zero to about 40 degrees C. In Scheme 14, "Tf" represents trifluoromethanesulfonyl, i.e., —$SO_2$—$CF_3$.

Scheme 14

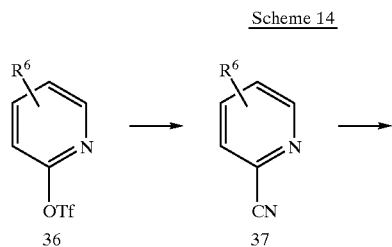

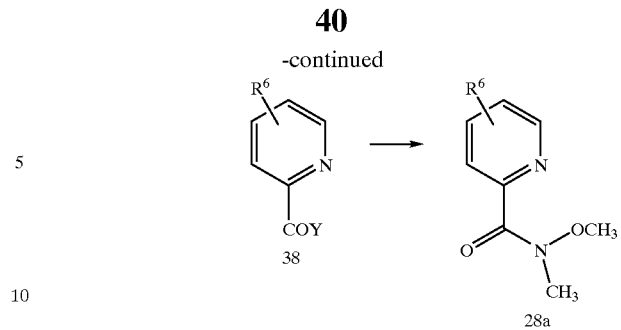

The compounds of formula 1 and some of the intermediates described above may have one or more stereogenic centers in their structure. Such stereogenic centers may be present in a R or a S configuration. Oxime moieties, such as where $R^3$, $R^4$, $R^5$, $R^6$ or $R^7$ is —CH=$NOR^{12}$, may exist in E or Z configurations.

The compounds of formula 1 as prepared in the above processes are generally racemic mixtures of enantiomers which can be separated from one another following resolution procedures familiar to those skilled in the art. The racemic compounds of formula 1 may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomerics forms of the compounds of formula 1 involves liquid chromatography using a chiral stationary phase. Said pure stereochemically isomeric forms may also be derived from the corresponding pure stereochemically isomeric forms of the appropriate starting materials, provided that the reaction occurs sterospecifically. Preferably if a specific stereoisomer is desired, said compound will be synthesized by stereospecfic methods of preparation. These methods will advantageously employ enantiomerically pure starting materials.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of formula 1 are similarly prepared except through reaction of a carboxy group with an appropriate cationic salt reagent, such as sodium, potassium, calcium, magnesium, ammonium, N,N'-dibenzylethylenediamine, N-methylglucamine (meglumine), ethanolamine, tromethamine, or diethanolamine.

The compounds of formula 1, 12, and 6 and their pharmaceutically acceptable salts and solvates (hereinafter referred to, collectively, as "the therapeutic compounds")

can be administered orally, transdermally (e.g., through the use of a patch), parenterally or topically. Oral administration is preferred. In general, compounds of the formula 1, 12, and 6 and their pharmaceutically acceptable salts and solvates are most desirably administered in dosages ranging from about 1.0 mg up to about 500 mg per day, preferably from about 1 to about 100 mg per day in single or divided (i.e., multiple) doses. The therapeutic compounds will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to in animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

For the combination therapies and pharmaceutical compositions described herein, the effective amounts of the compound of the invention and of the chemotherapeutic or other agent useful for inhibiting abnormal cell growth (e.g., other antiproliferative agent, anti-agiogenic, signal transduction inhibitor or immune-system enhancer) can be determined by those of ordinary skill in the art, based on the effective amounts for the compound described herein and those known or described for the chemotherapeutic or other agent. The formulations and routes of administration for such therapies and compositions can be based on the information described herein for compositions and therapies comprising the compound of the invention as the sole active agent and on information provided for the chemotherapeutic or other agent in combination therewith.

The compounds of formula 1 exhibit activity as Ras farnesylation inhibitors and are useful in the treatment of cancer and the inhibition of abnormal cell growth in mammals, including humans. The activity of the compounds of formula 1 as Ras farnesylation inhibitors may be determined by their ability, relative to a control, to inhibit Ras farnesyl transferase in vitro. An example of one such procedure is described below.

A crude preparation of human farnesyl transferase (FTase) comprising the cytosolic fraction of homogenized brain tissue is used for screening compounds in a 96-well assay format. The cytosolic fraction is prepared by homogenizing approximately 40 grams of fresh tissue in 100 ml of sucrose/$MgCl_2$/EDTA buffer (using a Dounce homogenizer; 10–15 strokes), centrifuging the homogenates at 1000 g for 10 minutes at 4° C., re-centrifuging the supernatant at 17,000 g for 15 minutes at 4° C., and then collecting the resulting supernatant. This supernatant is diluted to contain a final concentration of 50 mM Tris HCl (pH 7.5), 5 mM DTT, 0.2 M KCl, 20 µM $ZnCl_2$, 1 mM PMSF and re-centrifuged at 178,000 g for 90 minutes at 4° C. The supernatant, termed "crude FTase" is assayed for protein concentration, aliquoted, and stored at −70° C.

The assay used to measure in vitro inhibition of human FTase is a modification of the method described by Amersham LifeScience for using their Farnesyl transferase (3H) Scintillation Proximity Assay (SPA) kit (TRKQ 7010). FTase enzyme activity is determined in a volume of 100 µl containing 50 mM N-(2-hydroxy ethyl)piperazine-N-(2-ethane sulfonic acid) (HEPES), pH 7.5, 30 mM $MgCl_2$, 20 mM KCl, 25 mM $Na_2HPO_4$, 5 mM dithiothreitol (DTT), 0.01% Triton X-100, 5% dimethyl sulfoxide (DMSO), 20 mg of crude FTase, 0.12 mM [3]-farnesyl pyrophosphate ([3H]-FPP; 36000 dpm/pmole, Amersham LifeScience), and 0.2 µM of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 150 μl of steptavidin-coated SPA beads (TRKQ 7010) per well and incubating the reaction mixture for 30 minutes at room temperature. The amount of radio-activity bound to the SPA beads is determined using a MicroBeta 1450 plate counter. Under these assay conditions, the enzyme activity is linear with respect to the concentrations of the prenyl group acceptor, Bt-KTKCVIS, and crude FTase, and inhibition of Bt-KTKCVIS interaction with Frase can be detected. The enzyme activity is saturating with respect to the prenyl donor, FPP. The assay reaction time is also in the linear range.

The test compounds are routinely dissolved in 100% DMSO. Inhibition of farnesyl transferase activity is determined by calculating percent incorporation of tritiated-farnesyl in the presence of the test compound versus its incorporation in control wells (absence of inhibitor). $IC_{50}$ values, that is, the concentration required to produce half maximal farnesylation of Bt-KTKCVIS, is determined from the dose-responses obtained.

All of the title compounds of formula 1 in the following Examples were assayed for their ability to inhibit the activity of human farnesyl transferase in vitro using the assay described above, and were found to have $IC_{50}$ values for inhibiting farnesylation of the biotinylated KTKCVIS-peptide of about less than or equal to 500 nM.

The following Examples are provided to illustrate aspects of the subject invention. They are not intended, nor should they be construed, to limit the invention as more fully described herein and set forth in the claims.

EXAMPLE 1

4-(3-Chloro-phenyl)-6-[(6-chloro-pyridin-3-yl)-hydroxy-(3-methyl-3H-imidazol-4-yl)-methyl]-1H-quinolin-2-one 1A. 5-Bromo-3-(3-chloro-phenyl)-benzo[c]isoxazole To a solution of sodium hydroxide (19.8 g, 495 mmol) in methanol (36 ml) was added 3-choloroacetonitrile (17.5 ml, 149 mmol) at 0° C. under an atmosphere of dry $N_2$. The mixture was stirred at 0° C. for 30 minutes, 1-bromo-4-nitrobenzene (20 g, 99 mmol) was added as a solid at the same temperature. The solution was stirred at room temperature for 3 hours and then heated to reflux for one. The reaction mixture was cooled to ambient temperature and the MeOH was removed under vacuum. The resulting red oil was partitioned between ethyl acetate (EtOAc) and water. The organic layer was washed with brine, dried over $MgSO_4$ and concentrated under vacuum to give a tan solid. The solid was suspended in MeOH and the title compound of 1A was precipitated as a yellow solid (17.3 g, 55.9 mmol, 56.7% yield) which was used without further purification.

1B. (2-Amino-5-bromo-phenyl)-(3-chloro-phenyl)-methanone

To a solution of the title compound of example 1A (22.14 g, 78.1 mmol) in THF (300 ml) was added 276 mL of titanium(III) chloride (10 wt. % solution in 20–30 wt. % hydrochloric acid (HCl)). The reaction mixture was stirred for 1.5 hours. The reaction mixture was then poured into ice water. THF was removed from the resulting heterogeneous solution. The aqueous mixture was extracted with dichloromethane (DCM). The DCM layer was successively washed with aqueous saturated $NaHCO_3$ and brine. The DCM layer was dried over $MgSO_4$, filtered and concentrated under vacuum to give the title compound of 1B as a bright yellow solid (21.86 g, 70.4 mmol, 98% yield). The solid was used without further purification.

1C. 6-Bromo-4-(3-chloro-phenyl)-1H-quinolin-2-one

The title compound of example 1B (21.86 g, 70.4 mmol) was suspended in anhydrous toluene (140 ml) under an atmosphere of dry $N_2$. To this solution was added sequentially 26.7 ml (282 mmol) of acetic anhydride ($Ac_2O$), 80 ml (56.3 mmol) of triethylamine ($NEt_3$) and 8.60 g (70.4 mmol) of 4-dimethylaminopyridine (DMAP). The reaction mixture was then heated to reflux and stirred at this temperature for 20 hours. The reaction mixture was cooled to ambient temperature and the precipitate was collected via suction filtration. The solid was washed with ethyl ether ($Et_2O$) and dried under vacuum to give the title compound of example 1C (21.57 g). The filtrate was evaporated and the residue was suspended in cold EtOAc to form a precipitate, providing additional 4.64 g of the title compound. A total of 20.21 g (60.4 mmol, 85.8% yield) of the title compound of example 1C was obtain, which was used without further purification.

1D. 6-Bromo-4-(3-chloro-phenyl)-2-methoxy-quinoline

The title compound of example 1C (6.45 g, 19.4 mmol) was suspended in DCM (30 ml) under an atmosphere of dry $N_2$. To this suspension, was added trimethyloxonium tetrafluoroborate (BF4OMe3, 2.99 g, 20.2 mmol). The reaction mixture was stirred at ambient temperature for 15 hours. It was then cooled at 0° C. and a 10% aqueous NaOH solution (40 ml) was added. The reaction mixture was allowed to warm to room temperature and stirred for six hours after which time it was partitioned between DCM and water. The DCM layer was washed with brine, dried over $MgSO_4$ and concentrated under vacuum to give 6.11 g of the crude product. It was purified via chromatography with DCM as the eluent to afford the title compound of example 1D as a yellow solid, 5.23 g (15 mmol, 78% yield).

CI-MS: m/z 348/350.

1E. [4-(3-Chloro-phenyl)-2-methoxy-quinolin-6-yl]-(6-chloro-pyridin-3-yl)-(3-methyl-3H-imidazol-4-yl)-methanol To a solution of the title compound of example 1D (1.47 g, 348.6 mmol) in THF (10 ml) was added n-butyl lithium (2.5 M in hexane, 1.58 ml) dropwise at –78° C. under an atmosphere of dry $N_2$. After stirring at –78° C. for 30 minutes, a solution of (6-chloro-pyridin-3-yl)-(3-methyl-3H-imidazol-4-yl)-methanone (582.7 mg, 2.64 mmol) in THF (10 ml) was added. The reaction mixture was allowed to warm to ambient temperature and stirred for 15 hours. To the mixture was added a saturated aqueous solution of ammonium chloride at 0° C. THF was removed from the resulting heterogeneous solution. The aqueous mixture was extracted with chloroform ($CHCl_3$). The organic layer was washed with brine, dried over $MgSO_4$ and concentrated under vacuum to yield the crude product. It was chromatographed on silica gel with MeOH-$CHCl_3$—$NH_4OH$ (2:98:0.2 to 5:95:0.5) as eluents to afford the title compound of example 1E as a yellow solid (943 mg, 1.92 mmol, 73% yield).

CI-MS: m/z 491.1, 493.1 [M+1].

1F. 4-(3-Chloro-phenyl)-6-[(6-chloro-pyridin-3-yl)-hydroxy-(3-methyl-3H-imidazol-4-yl)-methyl]-1H-quinolin-2-one To a solution of the title compound of example 1E (4.67 g, 9.53 mmol) in THF (340 ml) was added concentrated hydrogen chloride (HCl, 14 ml) dropwise. The mixture was heated at 60° C. for 5 hours. After cooling to room temperature, THF was removed. The aqueous solution was adjusted to pH=~9 with 40% aqueous NaOH and extracted with $CHCl_3$ several times. The combined organic layer was washed with brine, dried over $MgSO_4$ and concentrated under vacuum to yield the title compound of Example 1 as an off-white solid (2.46 g, 5.17 mmol, 54% yield).

CI-MS: m/z 476.8.

EXAMPLE 2

4-(3-Chloro-phenyl)-6-[(6-chloro-pyridin-3-yl)-hydroxy-(3-methyl-3H-imidazol-4-yl)-methyl]-1-methyl-1H-quinolin-2-one To a solution of 4-(3-chloro-phenyl)-6-[(6-chloro-pyridin-3-yl)-hydroxy-(3-methyl-3H-imidazol-4-yl)-methyl]-1H-quinolin-2-one (351 mg, 0.737 mmol) in THF (15 ml) was added a 40% aqueous NaOH (2 ml), benzyl-triethylammonium chloride (84 mg, 0.369 mmol) and a solution of methyl iodide (0.078 ml, 1.25 mmol) in THF (4 ml). The reaction mixture was stirred at ambient temperature for 4 hours after which time it was partitioned between $CHCl_3$ and water. The organic layer was washed with brine, dried over $MgSO_4$ and concentrated under vacuum to give the crude product. It was chromatographed on silica gel with $MeOH-CHCl_3-NH_4OH$ (2:98:0.2 to 5:95:0.5) as eluents to afford the title compound as a white solid (200.3 mg, 0.408 mmol, 55% yield).

CI-MS: m/z 491.1.

EXAMPLE 3

6-[Amino-(6-chloro-pyridin-3-yl)-(3-methyl-3H-imidazol-4-yl)-methyl]-4-(3-chloro-phenyl)-1-methyl-1H-quinolin-2-one 4-(3-Chloro-phenyl)-6-[(6-chloro-pyridin-3-yl)-hydroxy-(3-methyl-3H-imidazol-4-yl)-methyl]-1-methyl-1H-quinolin-2-one (2 g, 4.08 mmol) was dissolved in 25 ml of thionyl chloride ($SOCl_2$) and stirred at room temperature under an atmosphere of dry $N_2$ for 2 hours. Thiony chloride was removed under reduced pressure. The crude chloride was taken up in toluene and concentrated under vacuum. The resulting solid was dissolved in THF (20 mL) and to this solution was bubbled ammonia gas ($NH_3$) for 30 minutes. The reaction mixture was stirred at ambient temperature under an atmosphere of $NH_3$ for 15 hours. After removal of THF, the product mixture was partitioned between $CHCl_3$ and water. The organic layer was washed, dried over $MgSO_4$ and concentrated under vacuum to give a brown solid. This was chromatographed on silica gel with $CHCl_3$ then $MeOH-CHCl_3-NH_4OH$ (1:99:0.1) as eluents to afford the titled compound as a white solid (1.065 g, 2.02 mmol, 50% yield).

C.I. m/z 490.2, 492.2 [M+1].

EXAMPLE 4 AND EXAMPLE 5

Separation of the Enantiomers of 6-[amino-(6-chloro-pyridin-3-yl)-(3-methyl-3H-imidazol-4-yl)-methyl]-4-(3chloro-phenyl)-1-methyl-1H-quinolin-2-one The title compound of Example 3, 6-[amino-(4-chloro-phenyl)-(3-methyl-3H-imidazol-4-yl)-methyl]-4-(3-ethynyl-phenyl)-1-methyl-1H-quinolin-2-one (159 mg) was separated into its enantiomers and purified by high-performance liquid chromatography over CHIRALCEL™ OD (manufactured by Daicel Chemical Industries, LTD, Osaka, Japan) (2.2 cm×25 cm, 10 μm; eluent: Hexane/ethanol/methanol/diethylamine 80/10/10/0.02; 25° C.). Under these conditions, 28 mg of the faster eluting enantiomer A (Example 4) and 3 mg of the slower moving enantiomer B (Example 5) were obtained. Both enantiomers were >97% optically pure.

EXAMPLE 6

4-(3-Chloro-phenyl)-6-[(6-chloro-pyridin-3-yl)-hydroxy-(3-methyl-3H-imidazol-4-yl)-methyl]-1-cyclopropylmethyl-1H-quinolin-2-one To a solution of the title compound of example 1, 4-(3-chloro-phenyl)-6-[(6-chloro-pyridin-3-yl)-hydroxy-(3-methyl-3H-imidazol-4-yl)-methyl]-1H-quinolin-2-one (100 mg, 0.210 mmol) in DMF (2 ml) were added NaCl (8 mg), cesium carbonate ($Cs_2CO_3$, 103 mg, 0.315 mmol) and (bromomethyl)cyclopropane (0.041 ml, 0.420 mmol). The reaction mixture was stirred at ambient temperature for 15 hours. Additional 0.041 ml) of (bromomethyl)cyclopropane and 100 mg of $Cs_2CO$ were added. The reaction mixture was heated at 60° C. for 1 hour after which time it was partitioned between $CHCl_3$ and water. The organic layer was washed with brine, dried over $MgSO_4$ and concentrated under vacuum to give the crude product. It was chromatographed on silica gel with $MeOH-CHCl_3-NH_4OH$ (3:97:0) as eluents to afford the title compound as a white solid (25 mg, 22% yield).

CI-MS: m/z 531.1, 533.1 [M+1].

EXAMPLE 7

6-[Amino-(6-Chloro-pyridin-3-yl)-(3-methyl-3H-imidazol-4-yl)-methyl]-4-(3-chloro-phenyl)-1-cyclopropylmethyl-1H-quinolin-2-one The same procedure was used as that in example 3, except that 4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one (400 mg, 0.75 mmol) was used in the place of 4-(3-chloro-phenyl)-6-[(6-chloro-pyridin-3-yl)-hydroxy-(3-methyl-3H-imidazol-4-yl)-methyl]-1-methyl-1H-quinolin-2-one, to give title compound as a white solid, 137 mg (0.26 mmol, 34% yield).

C.I. m/z 530.1, 532.1 [M+1].

EXAMPLE 8

4-(3-Chloro-phenyl)-6-[(6-chloro-pyridin-3-yl)-hydroxy-(3-methyl-3H-imidazol-4-yl)-methyl]-1-isobutyl-1H-quinolin-2-one Following the same procedure as described in Example 6, 1-bromo-2-methylpropane (0.041 ml, 0.42 mmol) was used in the place of (bromomethyl)cyclopropane. The alkylation of 4-(3-chloro-phenyl)-6-[6-chloro-pyridin-3-yl)-hydroxy-(3-methyl-3H-imidazol-4-yl)-methyl]-1-cyclopropylmethyl-1H-quinolin-2-one (99.8 mg, 0.21 mmol afforded the title compound as a white solid, 20 mg (0.038 mmol, 18% yield).

C.I. m/z 533.1, 535.1 M+1].

EXAMPLE 9

4-(3-Chloro-phenyl)-6-[(5-chloro-pyridin-2-yl)-hydroxy-(3-methyl-3H-imidazol-4-yl)-methyl]-1H-quinolin-2-one Following the same procedure as that described in example 1E, 6-bromo-4-(3-chloro-phenyl)-2-methoxy-quinoline (2.89 g, 8.31 mmol) and (5-chloro-pyridin-2-yl)-(3-methyl-3H-imidazol-4-yl)-methanone (1.47 g, 6.65 mmol) generated 4.05 g of the crude [4-(3-chloro-phenyl)-2-methoxy-quinolin-6-yl]-(6-chloro-pyridin-3-yl)-(3-methyl-3H-imidazol-4-yl)-methanol.

Following the same procedure as described in example 1F, the obtained [4-(3-chloro-phenyl)-2-methoxy-quinolin-6-yl]-(6-chloro-pyridin-3-yl)-(3-methyl-3H-imidazol-4-yl)-methanol was treated with HCl in aqueous THF to yield the title compound, 1.02 g, (2.14 mmol, 26% yield).

C.I. m/z 477.1, 479.1 [M+1].

EXAMPLE 10

4-(3-Chloro-phenyl)-6-[(5-chloro-pyridin-2-yl)-hydroxy-(3-methyl-3H-imidazol-4-yl)-methyl]-1-methyl-1H-quinolin-2-one The same procedure was used that described in example 2, except that 4-(3-chloro-phenyl)-6-[(5-chloro-pyridin-2-yl)-hydroxy-(3-methyl-3H-imidazol-4-yl)-methyl]-1H-quinolin-2-one (230 mg, 0.485 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give the title compound as a white solid, 195 mg (0.40 mmol, 81% yield).

EXAMPLE 11

6-[Amino-(5-chloro-pyridin-2-yl)-(3-methyl-3H-imidazol-4-yl)-methyl]-4-(3-chloro-phenyl)-1-methyl-1H-quinolin-2-one The same procedure was used as that described in example 3, 4-(3-chloro-phenyl)-6-[(5-chloro-pyridin-2-yl)-hydroxy-(3-methyl-3H-imidazol-4-yl)-methyl]-1-cyclopropylmethyl-1H-quinolin-2-one (170 mg, 0.35 mmol) was used in the place of 4-(3-Chloro-phenyl)-6-[(6-chloro-pyridin-3-yl)-hydroxy-(3-methyl-3H-imidazol-4-yl)-methyl]-1-methyl-1H-quinolin-2-one to give the title compound as a white solid, 69 mg (0.14 mmol, 40% yield).

C.I. m/z 490.0 [M+1].

EXAMPLE 12

4-(3-Chloro-phenyl)-6-[(5-chloro-pyridin-2-yl)-hydroxy-(3-methyl-3H-imidazol-4-yl)-methyl]-1-cyclopropylmethyl-1H-quinolin-2-one The same was used as that described in example 6, except that 4-(3-chloro-phenyl)-6-[(5-chloro-pyridin-2-yl)-hydroxy-(3-methyl-3H-imidazol-4-yl)-methyl]-1H-quinolin-2-one (550 mg, 1.16 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one, to give the title compound, 57 mg, (0.11 mmol, 9% yield).

C.I. m/z 531.1 [M+1].

EXAMPLE 13

6-[Amino-(5-chloro-pyridin-2-yl)-(3-methyl-3H-imidazol-4-yl)-methyl]-4-(3-chloro-phenyl)-1-cyclopropylmethyl-1H-quinolin-2-one The same procedure was used as that in example 3, except that 4-(3-chloro-phenyl)-6-[(5-chloro-pyridin-2-yl)-hydroxy-(3-methyl-3H-imidazol-4-yl)-methyl]-1-cyclopropylmethyl-1H-quinolin-2-one (258 mg, 0.486 mmol was used in the place of 4-(3-chloro-phenyl)-6-[(6-chloro-pyridin-3-yl)-hydroxy-(3-methyl-3H-imidazol-4-yl)-methyl]-1-methyl-1H-quinolin-2-one, to give the title compound as a white solid, 112 mg (0.21 mmol, 43% yield).

C.I. m/z 530.0 [M+1].

EXAMPLE 14

4-(3-Chloro-phenyl)-6-[(5-chloro-pyridin-2-yl)-cyclopropylamino-(3-methyl-3H-imidazol-4-yl)-methyl]-1-methyl-1H-quinolin-2-one For the formation of the correspondent chloride, the same procedure was used as that in example 2, except that 4-(3-chloro-phenyl)-6-[(5-chloro-pyridin-2-yl)-hydroxy-(3-methyl-3H-imidazol-4-yl)-methyl]-1-methyl-1H-quinolin-2-one (55 mg, 0.112 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one. The obtained chloride was dissolved in DMF (8 ml). To this solution were added potassium carbonate ($K_2CO_3$) and cyclopropylamine (0.049 ml, 0.786 mmol). The reaction mixture was stirred at ambient temperature for 15 hours after which time it was partitioned between $CHCl_3$ and water. The organic layer was washed with brine, dried over $MgSO_4$ and concentrated under vacuum to give the crude product. It was chromatographed on silica gel with $MeOH$-$CHCl_3$—$NH_4OH$ (2:98:0.2 to 5:95:0.5) as eluents to afford the title compound as a white solid (19 mg, 0.036 mmol, 32% yield).

C.I. m/z 529.9 [M+1].

EXAMPLE 15

4-(3-Chloro-phenyl)-6-[(5-chloro-pyridin-2-yl)-cyclopropylamino-(3-methyl-3H-imidazol-4-yl)-methyl]-1-cyclopropylmethyl-1H-quinolin-2-one The same procedure was used as that in example 14, except that 4-(3-Chloro-phenyl)-6-[(5-chloro-pyridin-2-yl)-hydroxy-(3-methyl-3H-imidazol-4-yl)-methyl]-1-cyclopropylmethyl-1H-quinolin-2-one (52 mg, 0.098 mmol) was used in the place of 4-(3-chloro-phenyl)-6-[(5-chloro-pyridin-2-yl)-hydroxy-(3-methyl-3H-imidazol-4-yl)-methyl]-1-methyl-1H-quinolin-2-one to give the title compound as a white solid (24 mg, 0.042 mmol, 43% yield).

C.I. m/z 569.9 [M+1].

EXAMPLE 16

6-[(6-Chloro-pyridin-3-yl)-hydroxy-(3-methyl-3H-imidazol-4-yl)-methyl]-4-(3,5-dichloro-phenyl)-1-methyl-1H-quinolin-2-one 16A. 6-Bromo-4-(3,5-dichloro-phenyl)-1H-quinolin-2-one The same procedure was used as that in example 1C, except that (2-amino-5-bromo-phenyl)-(3,5-dichloro-phenyl)-methanone (1.50 g, 4.35 mmol) was used in the place of (2-amino-5-bromo-phenyl)-(3-chloro-phenyl)-methanone to give the title compound of 16A as a white solid, 1.61 g (100% yield).

16B. 6-Bromo-4-(3,5-dichloro-phenyl)-2-methoxy-quinoline

The same procedure was used as that in example 1D, except that 6-bromo-4-(3,5-dichloro-phenyl)-1H-quinolin-2-one (6.42 g, 17.4 mmol) was used in the place of 6-bromo-4-(3-chloro-phenyl)-1H-quinolin-2-one to give the title compound of 16B as a white solid, 3.47 g (52% yield).

16C. [4-(3,5-Dichloro-phenyl)-2-methoxy-quinolin-6-yl]-(6-chloro-pyridin-3-yl)-(3-methyl-3H-imidazol-4-yl)-methanol Following the same procedure as described in example 1E, 6-bromo-4-(3,5-dichloro-phenyl)-2-methoxy-quinoline (1.88 g, 4.91 mmol) and (6-chloro-pyridin-3-yl)-(3-methyl-3H-imidazol-4-yl)-methanone (0.94 g, 4.27 mmol) generated the title compound of 16C as a yellow solid (0.885 g, 39.5% yield).

16D. 4-(3,5-Dichloro-phenyl)-6-[(6-chloro-pyridin-3-yl)-hydroxy-(3-methyl-3H-imidazol-4-yl)-methyl]-1H-quinolin-2-one Following the same procedure as described in example 1F, [4-(3,5-dichloro-phenyl)-2-methoxy-quinolin-6-yl]-(6-chloro-pyridin-3-yl)-(3-methyl-3H-imidazol-4-yl)-methanol (886 mg, 1.68 mmol) was treated with HCl in aqueous THF to yield the title compound of 16D. It was directly used for the next reaction without further purification.

16E. 6-[(6-Chloro-pyridin-3-yl)-hydroxy-(3-methyl-3H-imidazol-4-yl)-methyl]-4-(3,5-dichloro-phenyl)-1-methyl-1H-quinolin-2-one The same procedure was used as that in example 2, except that 4-(3,5-dichloro-phenyl)-6-[(6-chloro-pyridin-3-yl)-hydroxy-(3-methyl-3H-imidazol-4-yl)-methyl]-1H-quinolin-2-one (~1.68 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give the title compound of 16E as a white solid, 388.6 mg (44% yield for 16D and 16E).

C.I. m/z 525.0, 527.0 [M+1].

EXAMPLE 17

6-[Amino-(6-chloro-pyridin-3-yl)-(3-methyl-3H-imidazol-4-yl)-methyl]-4-(3,5-dichloro-phenyl)-1-methyl-1H-quinolin-2-one The same procedure was used as that in example 3, except that 6-[(6-chloro-pyridin-3-yl)-hydroxy-(3-methyl-3H-imidazol-4-yl)-methyl]-4-(3,5-dichloro-phenyl)-1-methyl-1H-quinolin-2-one (298.6 mg, 0.567 mmol) was used in the place of 4-(3-chloro-phenyl)-6-[(6-chloro-pyridin-3-yl)-hydroxy-(3-methyl-3H-imidazol-4-yl)-methyl]-1-methyl-1H-quinolin-2-one, to give the title compound as a white solid, 40 mg (0.076 mmol, 13% yield).

C.I. m/z 523.9, 526.0 [M+1].

EXAMPLE 18

4-(3-Chloro-phenyl)-6-[(5-chloro-thiophen-2-yl)-hydroxy-(3-methyl-3H-imidazol-4-yl)-methyl]-1-methyl-1H-quinolin-2-one 18A. [4-(3-Chloro-phenyl)-2-methoxy-quinolin-6-yl]-(5-chloro-thiophen-2-yl)-(3-methyl-3H-imidazol-4-yl)-methanol Following the same procedure as described in example 1E, 6-bromo-4-(3-chloro-phenyl)-2-methoxy-quinoline (1.0 g, 1.87 mmol) and (5-chloro-thiophen-2-yl)-(3-methyl-3H-imidazol-4-yl)-methanone (170 mg, 3.44 mmol) generated the title compound of 18A as a yellow solid (919 mg, 65% yield).

C.I. m/z 507.1 [M+1].

18B. 4-(3-Chloro-phenyl)-6-[(5-chloro-thiophen-2-yl)-hydroxy-(3-methyl-3H-imidazol-4-yl)-methyl]-1H-quinolin-2-one Following the same procedure as described in example 1F, [4-(3-chloro-phenyl)-2-methoxy-quinolin-6-yl]-(5-chloro-thiophen-2-yl)-(3-methyl-3H-imidazol-4-yl)-methanol (740 mg, 1.49 mmol) was treated with HCl in aqueous THF to yield the title compound of 18B as a yellow solid, 469.2 mg (0.97 mmol, 65% yield).

C.I. m/z 483.9 [M+1].

18C. 4-(3-Chloro-phenyl)-6-[(5-chloro-thiophen-2-yl)-hydroxy-(3-methyl-3H-imidazol-4-yl)-methyl]-1-methyl-1H-quinolin-2-one The same procedure was used as that in example 2, except that 4-(3-chloro-phenyl)-6-[(5-chloro-thiophen-2-yl)-hydroxy-(3-methyl-3H-imidazol-4-yl)-methyl-1H-quinolin-2-one (76 mg, 0.157 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give the title compound as a white solid, 49 mg (0.10 mmol, 63% yield)

C.I. m/z 497.9 [M+1].

EXAMPLE 19

6-[Amino-(5-chloro-thiophen-2-yl)-(3-methyl-3H-imidazol-4-yl)-methyl]-4-(3-chloro-phenyl)-1-methyl-1H-quinolin-2-one The same procedure was used as that in example 3, except that 4-(3-chloro-phenyl)-6-[(5-chloro-thiophen-2-yl)-hydroxy-(3-methyl-3H-imidazol-4-yl)-methyl]-1-methyl-1H-quinolin-2-one (69 mg, 0.139 mmol) was used in the place of 4-(3-chloro-phenyl)-6-[(6-chloro-pyridin-3-yl)-hydroxy-(3-methyl-3H-imidazol-4-yl)-methyl]-1-methyl-1H-quinolin-2-one, to give the title compound as a white solid, 14 mg (0.028 mmol, 20% yield).

C.I. m/z 523.9, 526.0 [M+1].

EXAMPLE 20

4-(3-Chloro-phenyl)-6-[(5-chloro-thiophen-2-yl)-hydroxy-(3-methyl-3H-imidazol-4-yl)-methyl]-1-cyclopropylmethyl-1H-quinolin-2-one The same was used as that described in example 6, except that 4-(3-chloro-phenyl)-6-[(5-chloro-thiophen-2-yl)-hydroxy-(3-methyl-3H-imidazol-4-yl)-methyl]-1-methyl-1H-quinolin-2-one (75 mg, 0.155 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one, to give the title compound (15 mg, 20% yield).

C.I. m/z 536.2, 538.2 [M+1].

EXAMPLE 21

4-(3-Chloro-phenyl)-6-[(3-chloro-thiophen-2-yl)-hydroxy-(3-methyl-3H-imidazol-4-yl)-methyl]-1-methyl-1H-quinolin-2-one 21A. [4-(3-Chloro-phenyl)-2-methoxy-quinolin-6-yl]-(3-chloro-thiophen-2-yl)-(3-methyl-3H-imidazol-4-yl)-methanol Following the same procedure as described in example 1E, 6-bromo-4-(3-chloro-phenyl)-2-methoxy-quinoline (300 mg, 0.859 mmol) and (3-chloro-thiophen-2-yl)-(3-methyl-3H-imidazol-4-yl)-methanone (230 mg, 1.032 mmol) generated the title compound of 21A as a yellow solid (218.5 mg, 51% yield).

21B. 4-(3-Chloro-phenyl)-6-[(3-chloro-thiophen-2-yl)-hydroxy-(3-methyl-3H-imidazol-4-yl)-methyl]-1H-quinolin-2-one Following the same procedure as described in example 1F, [4-(3-chloro-phenyl)-2-methoxy-quinolin-6-yl]-(3-chloro-thiophen-2-yl)-(3-methyl-3H-imidazol-4-yl)-methanol (208 mg, 0.42 mmol) was treated with HCl in aqueous THF to yield the title compound of 21B as a yellow solid (164.7 mg, 81% yield).

21C. 4-(3-Chloro-phenyl)-6-[(3-chloro-thiophen-2-yl)-hydroxy-3-methyl-3H-imidazol-4-yl)-methyl]-1-methyl-1H-quinolin-2-one The same procedure was used as that in example 2, except that 4-(3-chloro-phenyl)-6-[(3-chloro-thiophen-2-yl)-hydroxy-(3-methyl-3H-imidazol-4-yl)-methyl]-1H-quinolin-2-one (164.7 mg, 0.342 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give the title compound as a white solid (70 mg, 41% yield).

C.I. m/z [M+1].

EXAMPLE 22

6-[Amino-(3-chloro-thiophen-2-yl)-(3-methyl-3H-imidazol-4-yl)-methyl]-4-(3-chloro-phenyl)-1-methyl-1H-quinolin-2-one The same procedure was used as that in example 3, except that 4-(3-chloro-phenyl)-6-[(3-chloro-thiophen-2-yl)-hydroxy-(3-methyl-3H-imidazol-4-yl)-methyl]-1-methyl-1H-quinolin-2-one (65 mg, 0.13 mmol) was used in the place of 4-(3-chloro-phenyl)-6-[(6-chloro-pyridin-3-yl)-hydroxy-(3-methyl-3H-imidazol-4-yl)-methyl]-1-methyl-1H-quinolin-2-one, to give the title compound as a white solid (4.7 mg, 7% yield).

C.I. m/z 459.0 [M+1].

EXAMPLE 23

6-[(5-Chloro-thiophen-2-yl)-hydroxy-(3-methyl-3H-imidazol-4-yl)-methyl]-4-(3-ethoxy-phenyl)-1H-quinolin-2-one 23A. 6-Bromo-4-(3-ethoxy-phenyl)-2-methoxy-quinoline To a suspension of 6-bromo-4-(3-ethoxy-phenyl)-1H-quinolin-2-one (7.4 g, 21.5 mmol) in 60 ml dichloroethane was added trimethyloxonium tetrafluoroborate ($BF_4OMe_3$, 3.66 g, 24.7 mmol). The resulting mixture was stirred at ambient temperature overnight. After cooling to 0 C, was added 60 ml of 10% aqueous NaOH dropwise. The reaction mixture was stirred for another six hours at ambient temperature. It was then partitioned between dichloromethane and water. The organic layer was washed brine, dried over $MgSO_4$, filtered and concentrated under vacuum to give an off-white solid. The solid was chromatographed on flash silica gel eluting with dichoromethane to yield the titled compound of 23A as a white solid (4.48 g, 58% yield).

23B. (5-Chloro-thiophen-2-yl)-[4-(3-ethoxy-phenyl)-2-methoxy-quinolin-6-yl]-(3-methyl-3H-imidazol-4-yl)-methanol Following the same procedure as that described in example 1E, 6-bromo-4-(3-ethoxy-phenyl)-2-methoxy-quinoline (800 mg, 2.23 mmol) and (5-chloro-thiophen-2-yl)-(3-methyl-3H-imidazol-4-yl)-methanone (610 mg, 2.68 mmol) generated the title compound of 23B (810 mg, 72% yield).

23C. 6-[(5-Chloro-thiophen-2-yl)-hydroxy-(3-methyl-3H-imidazol-4-yl)-methyl]-4-(3-ethoxy-phenyl)-1H-quinolin-2-one Following the same procedure as described in example 1F, (5-chloro-thiophen-2-yl)-[4-(3-ethoxy-phenyl)-2-methoxy-quinolin-6-yl]-(3-methyl-3H-imidazol-4-yl)-methanol (810 mg, 1.60 mmol) was treated with HCl in aqueous THF to yield the title compound (578 mg, 74% yield).

C.I. m/z 492.1[M+1].

EXAMPLE 24

6-[(5-Chloro-thiophen-2-yl)-hydroxy-(3-methyl-3H-imidazol-4-yl)-methyl]-4-(3-ethoxy-phenyl)-1-methyl-1H-quinolin-2-one The same procedure was used as that in example 2, except that 6-[(5-chloro-thiophen-2-yl)-hydroxy-(3-methyl-3H-imidazol-4-yl)-methyl]-4-(3-ethoxy-phenyl)-1H-quinolin-2-one (578.4 mg, 1.18 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give the title compound as a white solid (241 mg, 40.4% yield).

C.I. m/z 506.2 [M+1].

EXAMPLE 25

Amino-(5-chloro-thiophen-2-yl)-(3-methyl-3H-imidazol-4-yl)-methyl]-4-(3-ethoxy-phenyl)-1-methyl-1H-quinolin-2-one The same procedure was used as that in example 3, except that 6-[(5-chloro-thiophen-2-yl)-hydroxy-(3-methyl-3H-imidazol-4-yl)-methyl]-4-(3-ethoxy-phenyl)-1-methyl-1H-quinolin-2-one (240 mg, 0.47 mmol) was used in the place of 4-(3-chloro-phenyl)-6-[(6-chloro-pyridin-3-yl)-hydroxy-(3-methyl-3H-imidazol-4-yl)-methyl]-1-methyl-1H-quinolin-2-one, to give the title compound as a white solid (196 mg, 82% yield).

C.I. m/z 505.1, 507.2 [M+1].

EXAMPLE 26

6-[(6-Chloro-pyridin-3-yl)-hydroxy-(3-methyl-3H-imidazol-4-yl)-methyl]-4-(3-ethoxy-phenyl)-1H-quinolin-2-one 26A. (6-Chloro-pyridin-3-yl)-[4-(3-ethoxy-phenyl)-2-methoxy-quinolin-6-yl]-(3-methyl-3H-imidazol-4-yl)-methanol Following the same procedure as that described in example 1E, 6-bromo-4-(3-ethoxy-phenyl)-2-methoxy-quinoline (2 g, 5.59 mmol) and (6-chloro-pyridin-3-yl)-(3-methyl-3H-imidazol-4-yl)-methanone (1.48 g, 6.70 mmol) generated the title compound of 26A (1.458 g, 52% yield).

26B. 6-[(6-Chloro-pyridin-3-yl)-hydroxy-(3-methyl-3H-imidazol-4-yl)-methyl]-4-(3-ethoxy-phenyl)-1H-quinolin-2-one Following the same procedure as described in example 1F, (6-chloro-pyridin-3-yl)-[4-(3-ethoxy-phenyl)-2-methoxy-quinolin-6-yl]-(3-methyl-3H-imidazol-4-yl)-methanol (1.58 g 2.92 mmol) was treated with HCl in aqueous THF to yield the title compound (1.21 g, 85% yield).

C.I. m/z 487.2 [M+1].

EXAMPLE 27

6-[(6-Chloro-pyridin-3-yl)-hydroxy-(3-methyl-3H-imidazol-4-yl)-methyl]-4-(3-ethoxy-phenyl)-1-methyl-1H-quinolin-2-one The same procedure was used as that in example 2, except that 6-[(6-chloro-pyridin-3-yl)-hydroxy-(3-methyl-3H-imidazol-4-yl)-methyl]-4-(3-ethoxy-phenyl)-1H-quinolin-2-one (80.6 mg, 0.166 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give the title compound as a white solid (43 mg, 52% yield).

C.I. m/z 501.2 [M+1].

EXAMPLE 28

6-[Amino-(6-chloro-pyridin-3-yl)-(3-methyl-3H-imidazol-4-yl)-methyl]-4-(3-ethoxy-phenyl)-1-methyl-1H-quinolin-2-one The same procedure was used as that in example 3, except that 6-[(6-chloro-pyridin-3-yl)-hydroxy-(3-methyl-3H-imidazol-4-yl)-methyl]-4-(3-ethoxy-phenyl)-1-methyl-1H-quinolin-2-one (20 mg, 0.04 mmol) was used in the place of 4-(3-chloro-phenyl)-6-[(6-chloro-pyridin-3-yl)-hydroxy-(3-methyl-3H-imidazol-4-yl)-methyl]-1-methyl-1H-quinolin-2-one, to give the title compound as a white solid (4.5 mg, 22.5% yield).

C.I. m/z 501.2 [M+1].

EXAMPLE 29

6-[(6-Chloro-pyridin-3-yl)-hydroxy-(3-methyl-3H-imidazol-4-yl)-methyl]-4-(3-ethoxy-phenyl)-1-isobutyl-1H-quinolin-2-one The same procedure described in example 8, 6-[(6-chloro-pyridin-3-yl)-hydroxy-(3-methyl-3H-imidazol-4-yl)-methyl]-4-(3-ethoxy-phenyl)-1H-quinolin-2-one (50 mg, 0.103 mmol) and 1-bromo-2-methylpropane (0.022 ml, 0.206 mmol) generated the title compound as a white solid (24 mg, 40% yield).

C.I. m/z 543.3 [M+1].

EXAMPLE 30

6-[(6-Chloro-pyridin-3-yl)-hydroxy-(3-methyl-3H-imidazol-4-yl)-methyl]-1-cyclopropylmethyl-4-(3-ethoxy-phenyl)-1H-quinolin-2-one The same procedure described in example 8, 6-[(6-chloro-pyridin-3-yl)-hydroxy-(3-methyl-3H-imidazol-4-yl)-methyl]-4-(3-ethoxy-phenyl)-1H-quinolin-2-one (50 mg, 0.103 mmol) and (bromomethyl)cyclopropane (0.020 ml, 0.206 mmol) generated the title compound as a white solid (4 mg, 7% yield).

C.I. m/z 541.3 [M+1].

EXAMPLE 31

6-[(5-Chloro-thiophen-2-yl)-hydroxy-(3-methyl-3H-imidazol-4-yl)-methyl]-4-(3-methoxy-phenyl)-1-methyl-1H-quinolin-2-one 31A. (5-Chloro-thiophen-2-yl)-[2-methoxy-4-(3-methoxy-phenyl)-quinolin-6-yl]-(3-methyl-3H-imidazol-4-yl)-methanol Following the same procedure as that described in example 1E, 6-bromo-4-(3-methoxy-phenyl)-2-methoxy-quinoline (1 g, 2.91 mmol) and (5-chloro-thiophen-2-yl)-(3-methyl-3H-imidazol-4-yl)-methanone (0.78 g, 3.49 mmol) generated the title compound of 31A (1.147 g, 80.2% yield).

C.I. m/z 492.1 [M+1].

31B. 6-[(5-Chloro-thiophen-2-yl)-hydroxy-(3-methyl-3H-imidazol-4-yl)-methyl]-4-(3-methoxy-phenyl)-4H-quinolin-2-one Following the same procedure as described in example 1F (5-chloro-thiophen-2-y)-[4-(3-methoxy-phenyl)-2-methoxy-quinolin-6-yl]-(3-methyl-3H-imidazol-4-yl)-methanol (1.14 g, 2.34 mmol) was treated with HCl in aqueous THF to yield the title compound of 31B (1.12 g, 100% yield).

C.I. m/z 478.1 [M+1].

31C. 6-[(5-Chloro-thiophen-2-yl)-hydroxy-(3-methyl-3H-imidazol-4-yl)-methyl]-4-(3-methoxy-phenyl)-1-methyl-1H-quinolin-2-one The same procedure was used as that in example 2, except that 6-[(5-chloro-thiophen-2-yl)-hydroxy-(3-methyl-3H-imidazol-4-yl)-methyl]-4-(3-methoxy-phenyl)-1H-quinolin-2-one (1.12 g, 2.34 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give two compounds after chromatographic purification. The fraction with higher Rf value afforded the title compound of example 31 as a white solid (422 mg, 36.7% yield).

C.I. m/z 492.1 [M+1].

EXAMPLE 32

6-[(5-Chloro-thiophen-2-yl)-methoxy-(3-methyl-3H-imidazol-4-yl)-methyl]-4-(3-methoxy-phenyl)-1-methyl-1H-quinolin-2-one From the reaction of example 31C, the fraction with lower Rf value afforded the title compound of example 32 as a white solid (50 mg, 4.2% yield).

C.I. m/z 506.2 [M+1].

EXAMPLE 33

6-[Amino-(5-chloro-thiophen-2-yl)-(3-methyl-3H-imidazol-4-yl)-methyl]-4-(3-methoxy-phenyl)-1-methyl-1H-quinolin-2-one The same procedure was used as that in example 3, except that 6-[(5-chloro-thiophen-2-yl)-hydroxy-(3-methyl-3H-imidazol-4-yl)-methyl]-4-(3-methoxy-phenyl)-1-methyl-1H-quinolin-2-one (43 mg, 0.087 mmol) was used in the place of 4-(3-chloro-phenyl)-6-[(6-chloro-pyridin-3-yl)-hydroxy-(3-methyl-3H-imidazol-4-yl)-methyl]-1-methyl-1H-quinolin-2-one, to give the title compound as a white solid (18 mg, 42% yield).

C.I. m/z 493.1 [M+1].

EXAMPLE 34

6-[(6-Chloro-pyridin-3-yl)-hydroxy-(3-methyl-3H-imidazol-4-yl)-methyl]-4-(3-isopropoxy-phenyl)-1H-quinolin-2-one 34A. 3-(6-Bromo-2-methoxy-quinolin-4-yl)-phenol To a solution of 6-bromo-4-(3-methoxy-phenyl)-2-methoxy-quinoline (1.31 g, 3.81 mmol) in dichloromethane ($CH_2Cl_2$, 30 ml) was added a solution of BBr3 in $CH_2Cl_2$ (1M, 11.4 ml, 11.4 mmol) at 0° C. The reaction mixture was allowed to warm to room temperature and stirred for 4 hours. It was poured into water. The organic layer was washed with brine, dried over MgSO4 and concentratred to give the title compound of example 34A (640 mg, 41% yield).

34B. 6-Bromo-4-(3-isopropoxy-phenyl)-2-methoxy-quinoline

To a solution of the title compound of example 34A (460 mg, 1.39 mmol) in DMF (10 ml) were added cesium carbonate ($Cs_2CO_3$, 906 mg, 2.78 mmol) and isopropylbromide (0.458 ml, 4.88 mmol). The reaction mixture was stirred at ambient temperature for 15 hours. Additional 0.041 ml) of (bromomethyl)cyclopropane and 100 mg of Cs2CO3 were added. The reaction mixture was heated at 60° C. for 1 hour after which time it was partitioned between ethyl ether and water. The organic layer was washed with brine, dried over $MgSO_4$ and concentrated under vacuum to give the crude title compound of example 34B (458 mg, 89% yield).

CI-MS: m/z 372.1, 374.1 [M+1].

34C. 6-[(6-Chloro-pyridin-3-yl)-[4-(3-isopropoxy-phenyl)-2-methoxy-quinolin-6-yl]-(3-methyl-3H-imidazol-4-yl)-methanol Following the same procedure as that described in example 1E, 6-bromo-4-(3-isopropoxy-phenyl)-2-methoxy-quinoline (238.4 mg, 0.640 mmol) and (6-chloro-pyridin-3-yl)-(3-methyl-3H-imidazol-4-yl)-methanone (156 mg, 0.705 mmol) generated the title compound of 34C (80 mg, 24% yield).

34D. 6-[(6-Chloro-pyridin-3-yl)-hydroxy-(3-methyl-3H-imidazol-4-yl)-methyl]-4-(3-isopropoxy-phenyl)-1H-quinolin-2-one Following the same procedure as described in example 1F, 6-[(6-chloro-pyridin-3-yl)-[4-(3-isopropoxy-phenyl)-2-methoxy-quinolin-6-yl]-(3-methyl-3H-imidazol-4-yl)-methanol (75 mg, 0.14 mmol) was treated with HCl in aqueous THF to yield the title compound (20 mg, 27% yield).

C.I. m/z 581.0 [M+1].

EXAMPLE 35

6-[(5-Chloro-thiophen-2-yl)-hydroxy-(3-methyl-3H-imidazol-4-yl)-methyl]-4-(3-hydroxy-phenyl)-1-methyl-1H-quinolin-2-one Following the same procedure as that described in Example 34A, the title compound of example 31 (100 mg, 0.203 mmol) was treated with BBr3 in CH$_2$Cl$_2$ (1M, 1.02 ml, 1.02 mmol) to give the title compound (64 mg, 67% yield).

C.I. m/z 478.1 [M+1].

EXAMPLE 36

4-(3-Chloro-phenyl)-6-(hydroxy-di-pyridin-3-yl-methyl)-1-methyl-1H-quinolin-2-one 36A. [4-(3-Chloro-phenyl)-2-methoxy-quinolin-6-yl]-di-pyridin-3-yl-methanol Following the same procedure as that described in example 1E, 6-bromo-4-(3-methoxy-phenyl)-2-methoxy-quinoline (400 mg, 1.15 mmol) and di-pyridin-3-yl-methanone (232 mg, 1.26 mmol) generated the title compound of 36A (303 mg, 58% yield).

C.I. m/z 454.0, 456.0 [M+1].

36B. 4-(3-Chloro-phenyl)-6-(hydroxy-di-pyridin-3-yl-methyl)-1H-quinolin-2-one

Following the same procedure as described in example 1F, [4-(3-chloro-phenyl)-2-methoxy-quinolin-6-yl]-di-pyridin-3-yl-methanol (300 mg, 0.66 mmol) was treated with HCl in aqueous THF to yield the title compound (290 mg, 100% yield).

C.I. m/z 581.0 [M+1].

36C. 4-(3-Chloro-phenyl)-6-(hydroxy-di-pyridin-3-yl-methyl)-1-methyl-1H-quinolin-2-one The same procedure was used as that in example 2, except that 4-(3-chloro-phenyl)-6-(hydroxy-di-pyridin-3-yl-methyl)-1H-quinolin-2-one (78 mg, 0.178 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give the title compound of example 36C as a white solid (23 mg, 29% yield).

C.I. m/z 454.2 [M+1].

EXAMPLE 37

4-(3-Ethoxy-phenyl)-6-(hydroxy-di-pyridin-3-yl-methyl)-1-methyl-1H-quinolin-2-one 37A. [4-(3-Ethoxy-phenyl)-2-methoxy-quinolin-6-yl]-di-pyridin-3-yl-methanol Following the same procedure as that described in example 1E, 6-bromo-4-(3-ethoxy-phenyl)-2-methoxy-quinoline (400 mg, 1.11 mmol) and di-pyridin-3-yl-methanone (225 mg, 1.22 mmol) generated the title compound of 37A (212 mg, 41.2% yield).

C.I. m/z 464.1 [M+1].

37B. 4-(3-Ethoxy-phenyl)-6-(hydroxy-di-pyridin-3-yl-methyl)-1H-quinolin-2-one

Following the same procedure as described in example 1F, [4-(3-ethoxy-phenyl)-2-methoxy-quinolin-6-yl]-di-pyridin-3-yl-methanol (212 mg, 0.457 mmol) was treated with HCl in aqueous THF to yield the title compound (91 mg, 44.3% yield).

C.I. m/z 450.1 [M+1].

37C. 4-(3-Ethoxy-phenyl)-6-(hydroxy-di-pyridin-3-yl-methyl)-1-methyl-1H-quinolin-2-one The same procedure was used as that in example 2, except that 4-(3-ethoxy-phenyl)-6-(hydroxy-di-pyridin-3-yl-methyl)-1H-quinolin-2-one (91 mg, 0.202 mmol) was used in the place 4-(3-chloro-phenyl)-6-[(6-chloro-pyridin-4-yl)-hydroxy-(3-methyl-3H-imidazol-4-yl)-methyl]-1H-quinolin-2-one to give the title compound of example 37C as a white solid (12 mg, 13% yield).

C.I. m/z 464.1 [M+1].

EXAMPLE 38

4-(3-Chloro-phenyl)-6-[hydroxy-(3-methyl-3H-imidazol-4-yl)-quinolin-3-yl-methyl]-1-methyl-1H-quinolin-2-one 38A. [4-(3-Chloro-phenyl)-2-methoxy-quinolin-6-yl]-3-methyl-3H-imidazol-4-yl)-quinolin-3-yl-methanol Following the same procedure as that described in Example 1E, 6-bromo-4-(3-methoxy-phenyl)-2-methoxy-quinoline (233 mg, 0.668 mmol) and (quinolin-3-yl)-(3-methyl-3H-imidazol-4-yl)-methanone (232 mg, 1.26 mmol) generated the title compound of 38A (81 mg, 24% yield).

C.I. m/z 507.1 [M+1].

38B. 4-(3-Chloro-phenyl)-6-[hydroxy-(3-methyl-3H-imidazol-4-yl)-quinolin-3-yl-methyl]-1H-quinolin-2-one Following the same procedure as described in Example 1F, the title compound of 38A (81 mg, 0.16 mmol) was treated with HCl in aqueous THF to yield the title compound of example 38B (56.4 mg, 71% yield).

C.I. m/z 493.0, 495.0 [M+1].

38C. 4-(3-Chloro-phenyl)-6-[hydroxy-(3-methyl-3H-imidazol-4-yl)-quinolin-3-yl-methyl]-1-methyl-1H-quinolin-2-one The same procedure was used as that in example 2, except that 4-(3-chloro-phenyl)-6-[hydroxy-(3-methyl-3H-imidazol-4-yl)-quinolin-3-yl-methyl]-1H-quinolin-2-one (56.4 mg, 0.115 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give the title compound of example 38C as a white solid (31 mg, 53% yield).

C.I. m/z 507.2 [M+1].

EXAMPLE 39

6-[Amino-(3-methyl-3H-imidazol-4-yl)-quinolin-3-yl-methyl]-4-(3-chloro-phenyl)-1-methyl-1H-quinolin-2-one The same procedure was used as that in example 3, except that 4-(3-chloro-phenyl)-6-[hydroxy-(3-methyl-3H-imidazol-4-yl)-quinolin-3-yl-methyl]-1-methyl-1H-quinolin-2-one (26 mg, 0.0514 mmol) was used in the place of 4-(3-chloro-phenyl)-6-[(6-chloro-pyridin-3-yl)-hydroxy-(3-methyl-3H-imidazol-4-yl)-methyl]-1-methyl-1H-quinolin-2-one, to give the title compound as a white solid (8.3 mg, 32% yield).

C.I. m/z 506.2 [M+1].

EXAMPLE 40

4-(3-Chloro-phenyl)-6-[(5-chloro-thiophen-2-yl)-imidazol-1-yl-methyl]-1-methyl-1H-quinolin-2-one 40A. [4-(3-Chloro-phenyl)-2-methoxy-quinolin-6-yl]-(5-chloro-thiophen-2-yl)-methanone To a solution of 6-bromo-4-(3-chloro-phenyl)-2-methoxy-quinoline (500 mg, 1.43 mmol) in THF (2 ml) was added n-buthyl lithium (2.5 M in hexane, 0.63 ml, 1.58 mmol) dropwise at −78° C. under an atmosphere of dry N$_2$. After stirring at −78° C. for 30 minutes, a solution of 5-chloro-thiophene-2-carboxylic acid methoxy-methyl-amide (440 mg, 2.15 mmol) in THF (1 ml) was added. The reaction mixture was allowed to warm to ambient temperature and stirred for 15 hours. To the mixture was added a saturated aqueous solution of ammonium chloride at 0° C. THF was removed from the resulting heterogeneous solution. The aqueous mixture was extracted with chloroform (CHCl$_3$). The organic layer was washed with brine, dried over MgSO$_4$ and concentrated under vacuum to yield the crude product. It was chromatographed on silica gel with MeOH-CHCl$_3$NH$_4$OH (2:98:0.2 to 5:95:0.5) as eluents to afford the title compound of example 40A (273.5 mg, 46% yield).

CI-MS: m/z 414.0 [M +1].

40B. 4-(3-Chloro-phenyl)-6-(5-chloro-thiophene-2-carbonyl)-1-1H-quinolin-2-one

Following the same procedure as that in example 1F, [4-(3-chloro-phenyl)-2-methoxy-quinolin-6-yl]-(5-chlorothiophen-2-yl)-methanone (273 mg, 0.66 mmol) was treated with HCl in aqueous THF to give the title compound of example 40B as a white solid (145 mg, 53% yield).

C.I. m/z 413.0, 415.0 [M+1].

40C. 4-(3-Chloro-phenyl)-6-(5-chloro-thiophene-2-carbonyl)-1-methyl-1H-quinolin-2-one The same procedure was used as that in example 2, except that 4-(3-chloro-phenyl)-6-(5-chloro-thiophene-2-carbonyl)-1-1H-quinolin-2-one (56 mg, 0.14 mmol) was used in the in place of 4-(3-chloro-phenyl)-6-[(6-chloro-pyridin-3-yl)-hydroxy-(3-methyl-3H-imidazo]-4-yl)-methyl]-1H-quinolin-2-one to give the title compound of example 40C as a white solid (58 mg, 100% yield).

C.I. m/z 413.9 [M+1].

40D. 4-(3-Chloro-phenyl)-6-[(5-chloro-thiophen-2-yl)-hydroxy-methyl]-1-methyl-1H-quinolin-2-one To a suspension of 4-(3-chloro-phenyl)-6-(5-chloro-thiophene-2-carbonyl)-1-methyl-1H-quinolin-2-one (58 mg, 0.154 mmol) in MeOH (1 ml) was added sodium borohydride as solid (NaBH$_4$, 7 mg, 0.185 mmol) at 0° C. The reaction mixture was stirred at 0° C. for one hour after which time it was partitioned between chloroform and water. The organic layer was washed with brine, dried over MgSO$_4$ and concentrated under vacuum to give an off-white solid (49 mg, 78.5% yield).

40E. 6-[Chloro-(5-chloro-thiophen-2-yl)-methyl]-4-(3-chloro-phenyl)-1-methyl-1H-quinolin-2-one To a solution of 4-(3-chloro-phenyl)-6-[(5-chloro-thiophen-2-yl)-hydroxy-methyl]-1-methyl-1H-quinolin-2-one 49 mg, 0.12 mmol) in CH$_2$Cl$_2$ (0.5 ml) was added thionyl chloride dropwise. The reaction mixture was stirred at room temperature for four hours. Thionyl chloride was removed under reduced pressure. The crude chloride was taken up in toluene and concentrated under vacuum to give a yellow solid which was used without further purification.

40F. 4-(3-Chloro-phenyl)-6-[(5-chloro-thiophen-2-yl)-imidazol-1-yl-methyl]-1-methyl-1H-quinolin-2-one The crude product from example 40E was dissolved in acetonitrile (CH$_3$CN, 1 ml). To this solution were added imidazole (29 mg, 0.42 mmol) and K$_2$CO$_3$ (58 mg, 0.42 mmol). The mixture was refluxed for 15 hours after which time it was partitioned between chloroform and water. The organic layer was washed with brine, dried over MgSO$_4$ and concentrated under vacuum to give the crude product. It was chromatographed on silica gel with MeOH-CHCl$_3$—NH$_4$OH (2:98:0.2) as eluents to afford the title compound (17 mg, 30% yield for two steps).

CI-MS: m/z 398.0, 400.0 [M–C$_3$H$_3$N$_2$ (imidazole)].

EXAMPLE 41

6-[Benzo[b]thiophen-2-yl-hydroxy-(3-methyl-3H-imidazol-4-yl)-methyl]-4-(3-chloro-phenyl)-1-methyl-1H-quinolin-2-one 41A. Benzo[b]thiophen-2-yl-[4-(3-chloro-phenyl)-2-methoxy-quinolin-6-yl]-(3-methyl-3H-imidazol-4-yl)-methanol Following the same procedure as described in example 1E, 6-bromo-4-(3-chloro-phenyl)-2-methoxy-quinoline (273 mg, 0.784 mmol) and benzo[b]thiophen-2-yl-(3-methyl-3H-imidazol-4-yl)-methanone (247 mg, 1.01 mmol) generated the title compound of 41A (248 mg, 62% yield).

C.I. m/z 507.1 [M+1].

41B. 6-[Benzo[b]thiophen-2-yl-hydroxy-(3-methyl-3H-imidazol-4-yl)-methyl]-4-(3-chloro-phenyl)-1H-quinolin-2-one Following the same procedure as described in example 1F, benzo[b]thiophen-2-yl-[4-(3-chloro-phenyl)-2-methoxy-quinolin-6-yl]-(3-methyl-3H-imidazol-4-yl)-methanol (147.2 mg, 0.287 mmol) was treated with HCl in aqueous THF to yield the title compound of 41B as a yellow solid (40 mg, 28% yield).

41C. 6-[Benzo[b]thiophen-2-yl-hydroxy-(3-methyl-3H-imidazol-4-yl)-methyl]-4-(3-chloro-phenyl)-1-methyl-1H-quinolin-2-one The same procedure was used as that in example 2, except that 6-[benzo[b]thiophen-2-yl-hydroxy-(3-methyl-3H-imidazol-4-yl)-methyl]-4-(3-chloro-phenyl)-1H-quinolin-2-one (40 mg, 0.08 mmol) was used in the place of 4-(3-chloro-phenyl)-6-[(6-chloro-pyridin-3-yl)-hydroxy-(3-methyl-3H-imidazol-4-yl)-methyl]-1H-quinolin-2-one to give the title compound as a white solid (5.3 mg, 13% yield)

C.I. m/z 512.1 [M+1].

EXAMPLE 42

6-[Amino-(6-chloro-pyridin-3-yl)-(3-methyl-3H-imidazol-4-yl)-methyl]-4-(3-chloro-phenyl)-1H-quinolin-2-one To 6-Bromo-4-(3-chloro-phenyl)-2-methoxy-quinoline (20.95 g, 42.76 mmol) in toluene (150 ml) under an atmosphere of dry N$_2$ was added thionyl chloride (31.19 ml, 427 mmol) dropwise. The reaction mixture was heated at 85° C. for 15 hours. Solvent and the excess thionyl chloride were removed under reduced pressure. The crude chloride was taken up in toluene and concentrated under vacuum. The resulting solid was dissolved in THF (10 ml) and to this solution at −78° C. was bubbled ammonia gas (NH$_3$) for 10 minutes. The reaction mixture was stirred at ambient temperature under an atmosphere of N$_2$ for additional 1.5 hours. After removal of THF, the product mixture was partitioned between CHCl$_3$ and water. The organic layer was washed, dried over MgSO$_4$ and concentrated under vacuum to give the crude product. It was chromatographed on silica gel with CHCl$_3$ then MeOH-CHCl$_3$—NH$_4$OH (2:98:0.1 to 7:93:0.1) as eluents to afford the titled compound (17.89 g, 88% yield).

C.I. m/z 473.8 [M+1].

EXAMPLE 43

4-(3-Chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one 43A. 4-(3-Chloro-phenyl)-6-[(6-chloro-pyridin-3-yl)-[(4-methoxy-benzylidene)-amino]-(3-methyl-3H-imidazol-4-yl)-methyl]-1H-quinolin-2-one To a solution of the title compound of example 42 (11.89 g, 25.03 mmol) in acetic acid (75 ml) was added p-anisaldehyde (6.09 ml, 60.06 mmol) dropwise. The reaction mixture was stirred at ambient temperature for 4 hours after which time it was cooled to 0° C. 10 ml of ammonia hydroxide was added followed by addition of ethyl acetate. After separation, the organic layer was washed with brine, dried over MgSO$_4$ and concentrated under vacuum to yield the crude product. It was chromatographed on silica gel with MeOH-CHCl$_3$—NH$_4$OH (1:99:0.1 to 5:95:0.1) as eluents to afford the title compound of Example 43A as a white solid (11.58 g, 78% yield).

CI-MS: m/z 594.1, 596.1 [M+1].

43B. 4-(3-Chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one To a solution of the title compound of example 43A (10.78 g, 18.14 mmol) in THF (2.5 ml) was added (bromomethyl)cyclopropane (2.42 ml, 24.96 mmol), benzyltriethylammonium chloride (2.59 g, 11.34 mmol), sodium iodide (0.85 g, 5.67 mmol) and a solution of 40% aqueous NaOH (30 ml). The reaction mixture was heated at 65° C. for 4 hours after which time THF was removed. The crude product mixture was partitioned between $CHCl_3$ and water. The organic layer was washed with brine, dried over $MgSO_4$ and concentrated under vacuum to give the crude product. It was chromatographed on silica gel MeOH-$CHCl_3$—$NH_4OH$ (1.5:98.5:0.1 to) as the eluents to afford the title compound as a white solid (8.49 g, 13.10 mmol, 72% yield).

CI-MS: m/z 648.1 [M+1].

EXAMPLE 44 AND EXAMPLE 45

(+) and (−) Enantiomers of 4-(3-Chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one The title compound of Example 43 (1.322 g) was separated into its enantiomers and purified by high-performance liquid chromatography over CHIRALCEL™ OD (manufactured by Daicel Chemical Industries, LTD, Osaka, Japan) (2.2 cm×25 cm, 10 µm; eluent: Hexane/ethanol/methanol/diethylamine 80/10/10/0.1; 25° C.). Under these conditions, 0.595 g of the faster eluting enantiomer A (Example 44): (+)-4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one, and 0.511 g of the slower moving enantiomer B (Example 45): (−)-4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one were obtained. Both enantiomers were >99% optical pure.

EXAMPLE 46

4-(3-Chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one 46A. 4-(3-Chloro-phenyl)-6-[(6-chloro-pyridin-3-yl)-(4-methoxy-benzylamino)-(3-methyl-3H-imidazol-4-yl)-methyl]-1H-quinolin-2-one To 6-Bromo-4-(3-chloro-phenyl)-2-methoxy-quinoline (1.08 g, 2.21 mmol) in toluene (8.5 ml) under an atmosphere of dry $N_2$ was added thionyl chloride (1.61 ml, 22.06 mmol) dropwise. The reaction mixture was heated at 85° C. for 15 hours. Solvent and the excess thionyl chloride were removed under reduced pressure. The crude chloride was taken up in toluene and concentrated under vacuum. The resulting solid was dissolved in THF (10 ml) and to this solution at −78° C. was added p-methoxybenzylamine (i.44 ml, 11.03 mmol) in THF (2 ml). The reaction mixture was stirred at −78° C. for 3 hours under an atmosphere of $N_2$ for 3 hours. After removal of THF, the product mixture was partitioned between $CHCl_3$ and water. The organic layer was washed, dried over $MgSO_4$ and concentrated under vacuum to give the crude product. It was chromatographed on silica gel with MeOH-$CHCl_3$—$NH_4OH$ (2:98:0.1) as eluents to afford the titled compound of Example 46A (0.482 g, 52% yield).

C.I. m/z 596.1 [M+1].

46B. 4-(3-Chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one The same procedure was used as that described in example 43B, except that 4-(3-chloro-phenyl)-6-[(6-chloro-pyridin-3-yl)-(4-methoxy-benzylamino)-(3-methyl-3H-imidazol-4-yl)-methyl]-1H-quinolin-2-one (0.682 g, 1.14 mmol) was used in the place of 4-(3-chloro-phenyl)-6-[(6-chloro-pyridin-3-yl)-[(4-methoxy-benzylidene)-amino]-(3-methyl-3H-imidazol-4-yl)-methyl]-1H-quinolin-2-one to give the title compound (0.315 g, 0.485 mmol, 43% yield).

C.I. m/z 650.1 [M+1].

EXAMPLE 47 AND EXAMPLE 48

(+) and (−) Enantiomers of 4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one The title compound of Example 46, 4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one (3.05 g) was separated into its enantiomers and purified by high-performance liquid chromatography over CHIRALPAK™ AD (manufactured by Daicel Chemical Industries, LTD, Osaka, Japan) (2.2 cm×25 cm, 10 µm; eluent: Hexane/ethanol/methanol/diethylamine 80/10/10/0.1; 25° C.). Under these conditions, 1.56 g of the faster eluting enantiomer A (Example 47): (+)-4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one, and 1.07 g of the slower moving enantiomer B (Example 48): (−)-4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one were obtained. Both enantiomers were >99% optical pure.

EXAMPLE 49

(+)-6-[Amino-(6-chloro-pyridin-3-yl)-(3-methyl-3H-imidazol-4-yl)-methyl]-4-(3-chloro-phenyl)-1-cyclopropylmethyl-1 H-quinolin-2-one Procedure 1, Conversion of Example 45

To a solution of the title compound of Example 45, the slower moving enantiomer of 4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one (141 g, 1.74 mmol) in THF (200 ml) was added 2N hydrochloric acid (20 ml) slowly. The reaction mixture was stirred at ambient temperature for 1.5 hour after which time it was cooled to 0° C. An aqueous solution of potassium carbonate was added followed by addition of ethyl acetate. After separation, the organic layer was washed with brine, dried over $MgSO_4$ and concentrated under vacuum to give the crude product. It was chromatographed on silica gel with MeOH-$CHCl_3$—$NH_4OH$ (1:99:0.1 to 2:98:0.1) as the eluents to afford the title compound as a white solid (0.844 g, 1.59 mmol, 90% yield). It is the faster eluting enantiomer of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one with >99% optical purity.

C.I. m/z: 530.1, 532.1 [M+1].

Procedure 2, Conversion of Example 48

To a solution of the title compound of Example 48 (the slower moving enantiomer), (−)4-(3-chloro-phenyl)-6-[(6-chloro-pyridin-3-yl)-(4-methoxy-benzyl-amino)-(3-methyl-3H-imidazol-4-yl)-methyl]-1-cyclopropylmethyl-1H- quinolin-2-one (1.07 g, 1.64 mmol) in dichloromethane (6.5 ml) was added trifluoroacetic acid (TFA, 6.5 ml) slowly at 0° C. The reaction mixture was stirred at ambient temperature for 80 minutes after which time it was diluted with DCM (10 ml) and was poured into a chilled aqueous solution of potassium carbonate. After separation, the organic layer was washed with brine, dried over $MgSO_4$ and concentrated under vacuum to give the crude product. It was chromatographed on silica gel with $MeOH-CHCl_3—NH_4OH$ (1.5:98.5:0.15) as the eluents to afford the title compound as a white solid (0.588 g, 1.11 mmol, 68% yield). It is the faster eluting enantiomer of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one with >99% optical purity.

C.I. m/z: 530.1, 532.1 [M+1].

EXAMPLE 50

(–)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one Procedure 1, Conversion of Example 44

Following the same procedure as that described in Example 49 for the conversion of Example 45, the title compound of Example 44, the faster eluting enantiomer of 4-(3-chloro-phenyl)-6-[(6-chloro-pyridin-3-yl)-[(4-methoxy-benzylidene)-amino]-(3-methyl-3H-imidazol-4-yl)-methyl]-1-cyclopropylmethyl-1H-quinolin-2-one (1.98 g, 3.05 mmol) afforded the title compound as a white solid (1.51 g, 2.85 mmol, 93% yield). It is the slower moving enantiomer of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one with >99% optical purity.

C.I. m/z: 530.1, 532.1 [M+1].

Procedure 2, Conversion of Example 47

Following the same procedure as that described in Example 49 for the conversion of Example 48, the title compound of Example 47 (the faster eluting enantiomer, (+)-4-(3-chloro-phenyl)-6-[(6-chloro-pyridin-3-yl)-(4-methoxy-benzylamino)-(3-methyl-3H-imidazol-4-yl)-methyl]-1-cyclopropylmethyl-1H-quinolin-2-one (0.249 g, 0.384 mmol) afforded the title compound as a white solid (0.137 g, 0.252 mmol, 66% yield). It is the slower moving enantiomer of 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one with >98% optical purity.

C.I. m/z: 530.1, 532.1 [M+1].

EXAMPLE 51

6-[Amino-(6-methyl-pyridin-3-yl)-(3-methyl-3H-imidazol-4-yl)-methyl]-4-(3-chloro-phenyl)-1-methyl-1H-quinolin-2-one 51A. [4-(3-chloro-phenyl)-2-methoxy-quinolin-6-yl]-(6-methyl-pyridin-3-yl)-3-methyl-3H-imidazol-4-yl)-methanol.

Following the same procedure as that described in Example 1E, 6-bromo-4-(3-chloro-phenyl)-2-methoxy-quinoline (0.200 g, 0.574 mmol) and (6-methyl-pyridin-3-yl)-(3-methyl-3H-imidazol-4-yl)-methanone (0.105 g, 0.522 mmol) generated 0.118 g (48% yield) of [4-(3-chloro-phenyl)-2-methoxy-quinolin-6-yl]-(6-methyl-pyridin-3-yl)-(3-methyl-3H-imidazol-4-yl)-methanol.

C.I. m/z: 470.9[M+1].

51B. 6-[Amino-(6-methyl-pyridin-3-yl)-(3-methyl-3H-imidazol-4-yl)-methyl]-4-(3-chloro-phenyl)-1H-quinolin-2-one To the title compound of Example 51A (0.118 g, 0.251 mmol) in toluene (5 ml) under an atmosphere of dry $N_2$ was added thionyl chloride (0.18 ml, 2.51 mmol) dropwise. The reaction mixture was heated at 85° C. for 15 hours. Solvent and the excess thionyl chloride were removed under reduced pressure. The crude chloride was taken up in toluene and concentrated under vacuum. The resulting solid was dissolved in THF (10 mL) and to this solution at –78° C. was bubbled ammonia gas ($NH_3$) for 10 minutes. The reaction mixture was stirred at ambient temperature under an atmosphere of $N_2$ for additional 1.5 hours. After removal of THF, the product mixture was partitioned between $CHCl_3$ and water. The organic layer was washed, dried over $MgSO_4$ and concentrated under vacuum to give a brown solid. This was chromatographed on silica gel with CHCl then MeOH-$CHCl_3—NH_4OH$ (5:95:0.1 to 10:89:1) as eluents to afford the title compound of Example 51B as a white solid (53 mg, 0.116 mmol, 46.4% yield).

C.I. m/z 456.3 [M+1].

51C. 6-[Amino-(6-methyl-pyridin-3-yl)-(3-methyl-3H-imidazol-4-yl)-methyl]-4-(3-chloro-phenyl)-1-methyl-1H-quinolin-2-one To a solution of the title compound of Example 51B (26 mg, 0.057 mmol) in THF (2.5 ml) was added a solution of 40% aqueous NaOH (0.1 ml), benzyltriethylammonium chloride (6.5 mg, 0.074 mmol) and methyl iodide (0.0046 ml, 0.0743 mmol). The reaction mixture was stirred at ambient temperature for 3 hours after which time THF was removed. The crude product mixture was partitioned between $CHCl_3$ and water. The organic layer was washed with brine, dried over $MgSO_4$ and concentrated under vacuum to give the crude product. It was purified by thin layer chromatography with $MeOH-CHCl_3—NH_4OH$ (5:95:0.1) as the mobile phase to afford the title compound as a white solid (14.4 mg, 0.031 mmol, 54% yield).

CI-MS: m/z 470.0 [M+1].

EXAMPLE 52

6-[Amino-(6-methyl-pyridin-3-yl)-(3-methyl-3H-imidazol-4-yl)-methyl]-4-(3-chloro-phenyl)-1-cyclopropylmethyl-1H-quinolin-2-one To a solution of the title compound of Example 51B (26 mg, 0.057 mmol) in THF (2.5 ml) was added (bromomethyl)cyclopropane (0.0075 ml, 0.080 mmol), benzyltriethylammonium chloride (6.5 mg, 0.0286 mmol), sodium iodide (2.57 mg, 0.0171 mmol) and a solution of 40% aqueous NaOH (0.57 ml). The reaction mixture was heated at 65° C. for 3 hours after which time THF was removed. The crude product mixture was partitioned between $CHCl_3$ and water. The organic layer was washed with brine, dried over $MgSO_4$ and concentrated under vacuum to give the crude product. It was chromatographed on silica gel with $MeOH-CHCl_3—NH_4OH$ (2:98:0.1 to 5:95:0.1) as the eluents to afford the title compound as a white solid (11 mg, 0.022 mmol, 38% yield).

CI-MS: m/z 510.3 [M+1].

EXAMPLE 53

6-[Amino-(pyridin-3-yl)-(3-methyl-3H-imidazol-4-yl)-methyl]-4-(3-chloro-phenyl)-1-cyclopropylmethyl-1H-quinolin-2-one To a solution of the title compound of Example 7, 6-[amino-(6-chloro-pyridin-3-yl)-(3-methyl-3H-imidazol- 4-yl)-methyl]-4-(3-chloro-phenyl)-1-cyclopropylmethyl-1H-quinolin-2-one (0.408 g, 0.77 mmol) in pyridine (0.77 ml) was added trichloroethyl chloroformate (0.159 ml, 1.15 mmol) at 0° C. The reaction mixture was gradually warmed to room temperature and stirred overnight. After removal of pyridine, the product mixture was taken into dichloromethane and water. After separation, the organic layer was washed with brine, dried over $MgSO_4$ and concentrated under vacuum to give the crude product. It was chromatographed on silica gel with $MeOH-CHCl_3-NH_4OH$ (1:99:0.1) as the eluents to afford the trichloroethyl carbamate as a white solid (0.451 9, 0.64 mmol, 83% yield).

CI-MS: m/z 705.8, 708.0 [M+1].

To a solution of the trichloroethyl carbamate (34 mg, 0.048 mmol) in formic acid (0.96 ml) was added zinc powder (87 mg). The reaction mixture was stirred at ambient temperature for 15 minutes. After addition of methanol, the mixture was filtered through the celite, followed by a saturated solution of potassium carbonate. The filtrated was evaporated and was extracted with chloroform. The organic layer was washed with brine, dried over $MgSO_4$ and concentrated under vacuum to give the crude product. It was chromatographed on silica gel with $MeOH-CHCl_3-NH_4OH$ (2:98:0.) as the eluents to afford the title compound as a white solid (25 mg, 100% yield).

CI-MS: m/z 496.1 [M+1].

EXAMPLE 54 AND EXAMPLE 55

(+) and (−) Enantiomers of 4-(3-Chloro-phenyl)-6-[(6-chloro-pyridin-3-yl)-hydroxy-(3-methyl-3H-imidazol-4-yl)-methyl]-1-cyclopropylmethyl-1H-quinolin-2-one To a solution of the title compound of Example 43 (4.31 g, 6.64 mmol) in THF (30 ml) was added 38 ml of 1N sulfuric acid. After the mixture was cooled to 0° C., a solution of sodium nitrite ($NaNO_2$, 1.45 g, 20.99 mmol) in water (10 ml) was added dropwise. The reaction mixture was stirred at ambient temperature for 7 hours after which time ethyl acetate was added. The organic layer was washed with saturated potassium carbonate, brine, dried over $MgSO_4$ and concentrated under vacuum to give the crude product. It was chromatographed on silica gel with $MeOH-CHCl_3-NH_4OH$ (2:98:0.1) as the eluents to afford the title compound of Example 6, 4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one as a white solid (3.32 g, 94% yield).

CI-MS: m/z 530.9 [M+1].

(+/−)-4-(3-Chloro-phenyl)-6-[(6-chloro-pyridin-3-yl)-hydroxy-(3-methyl-3H-imidazol-4-yl)-methyl]-1-cyclopropylmethyl-1H-quinolin-2-one (3.002 g) was separated into its enantiomers and purified by high-performance liquid chromatography over CHIRALCEL™ OD (manufactured by Daicel Chemical Industries, LTD, Osaka, Japan) (2.2 cm×25 cm, 10 μm; eluent: Hexane/ethanol/methanol 85/7.5/7.5; 25° C.). Under these conditions, 1.14 g of the faster eluting enantiomer A, (Example 54): (−)-4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one and 0.7 g of the slower moving enantiomer B (Example 55): (+)-4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one were obtained.

Both enantiomers were >98% optically pure.

EXAMPLE 56

(+)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one, Dihydrochloride Salt To a solution of (+)-4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one (0.844 g, 1.59 mmol) in DCM (10 ml) was added a solution of HCl in ethyl ether (1M, 4,77 ml, 4.77 mmol). The slurry solution was stirred for 2 hours. After filtration, the title compound of example 56 was obtained as a white solid (0.78 g, 1.29 mmol, 81.4% yield).

EXAMPLE 57

(−)-6-[Amino-(6-chloro-pyridin-3-yl)-(3-methyl-3H-imidazol-4-yl)-methyl]-4-(3-chloro-phenyl)-1-cyclopropylmethyl-1H-quinolin-2-one, Dihydrochloride Salt Following the same procedure as that described in example 56, (−)-4-(3-chloro-phenyl)-6-[(6-chloro-pyridin-3-yl)-hydroxy-(3-methyl-3H-imidazol-4-yl)-methyl]-1-cyclopropylmethyl-1H-quinolin-2-one (0.252 g, 0.474 mmol) generated the dihydrochloride salt as a white solid (0.167 g, 0.28 mmol, 58% yield).

What is claimed is:

1. A method of synthesizing a compound of the formula

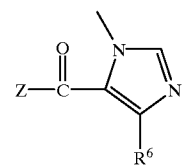

11a wherein $R^6$ is selected from H, $C_1-C_{10}$ alkyl, $C_2-C_{10}$ alkenyl, $C_2-C_{10}$ alkynyl, halo, cyano, nitro, trifluoromethyl, trifluoromethoxy, azido, $-OR^{12}$, $-C(O)R^{12}$, $-C(O)OR^{12}$, $-NR^{13}C(O)OR^{15}$, $-OC(O)R^{12}$, $-NR^{13}SO_2R^{15}$, $-SO_2NR^{12}R^{13}$, $-NR^{13}C(O)R^{12}$, $-C(O)NR^{12}R^{13}$, $-NR^{12}R^{13}$, $-CH=NOR^{12}$, $-S(O)_jR^{12}$ wherein j is an integer from 0 to 2, $-(CR^{13}R^{14})_t(C_6-C_{10}$ aryl), $-(CR^{13}R^{14})_t(4-10$ membered heterocyclic), $-(CR^{13}R^{14})_t(C_3-C_{10}$ cycloalkyl), and $-(CR^{13}R^{14})_tC\equiv CR^{16}$; and wherein the cycloalkyl, aryl and heterocyclic moieties of the foregoing groups are optionally fused to a $C_6-C_{10}$ aryl group, a $C_5-C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, $-NR^{13}SO_2R^{15}$, $-SO_2NR^{12}R^{13}$, $-C(O)R^{12}$, $-C(O)OR^{12}$, $-OC(O)R^{12}$, $-NR^{13}C(O)OR^{15}$, $-NR^{13}C(O)R^{12}$, $-C(O)NR^{12}R^{13}$, $-NR^{12}R^{13}$, $-OR^{12}$, $C_1-C_{10}$ alkyl, $C_2-C_{10}$ alkenyl, $C_2-C_{10}$ alkynyl, $-(CR^{13}R^{14})_t(C_6-C_{10}$ aryl), and $-(CR^{13}R^{14})_t(4-10$ membered heterocyclic);

Z is an aromatic 4–10 membered heterocyclic group, substituted by 1 to 4 $R^6$ substituents;

each $R^{12}$ is independently selected from H, $C_1-C_{10}$ alkyl, $-(CR^{13}R^{14})_t(C_3-C_{10}$ cycloalkyl), $-(CR^{13}R^{14})_t$ ($C_6$–$C_{10}$ aryl), and —$(CR^{13}R^{14})_t$(4–10 membered heterocyclic); said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;

each t is independently an integer from 0 to 5;

each $R^{13}$ and $R^{14}$ is independently H or $C_1$–$C_6$ alkyl, and where $R^{13}$ and $R^{14}$ are as —$(CR^{13}R^{14})_t$ each is independently defined for each iteration of t in excess of 1;

$R^{15}$ is selected from the substituents provided in the definition of $R^{12}$ except $R^{15}$ is not H;

$R^{16}$ is selected from the list of substituents provided in the definition of $R^{12}$ and —$SiR^{17}R^{18}R^{19}$; and, $R^{17}$, $R^{18}$ and $R^{19}$ are each independently selected from the substituents provided in the definition of $R^{12}$ except at least one of $R^{17}$, $R^{18}$ and $R^{19}$ is not H;

which method comprises reacting in an appropriate solvent in the presence of a suitable base a compound of the formula

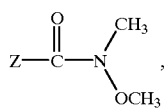

28 wherein Z is as defined above;

with a compound of the formula

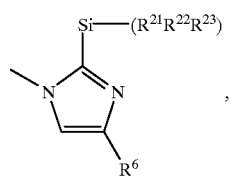

33 wherein $R^6$ is as defined above, and $R^{21}$, $R^{22}$, and $R^{23}$ are each independently selected from $C_1$–$C_6$ alkyl and phenyl;

thereby obtaining a compound of the formula

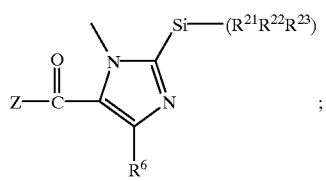

32 and reacting the compound of formula 32 so obtained in an appropriate solvent with acetic acid or with a fluoride reagent.

2. A method of synthesizing a compound of the formula

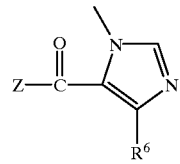

11a wherein $R^6$ is selected from H, $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —$OR^{12}$, —$C(O)R^{12}$, —$C(O)OR^{12}$, —$NR^{13}C(O)OR^{15}$, —$OC(O)R^{12}$, —$NR^{13}SO_2R^{15}$, —$SO_2NR^{12}R^{13}$, —$NR^{13}C(O)R^{12}$, —$C(O)NR^{12}R^{13}$, —$NR^{12}R^{13}$, —$CH=NOR^{12}$, —$S(O)_jR^{12}$ wherein j is an integer from 0 to 2, —$(CR^{13}R^{14})_t(C_6$–$C_{10}$ aryl), —$(CR^{13}R^{14})_t$(4–10 membered heterocyclic), —$(CR^{13}R^{14})_t(C_3$–$C_{10}$ cycloalkyl), and —$(CR^{13}R^{14})_tC\equiv CR^{16}$; and wherein the cycloalkyl, aryl and heterocyclic moieties of the foregoing groups are optionally fused to a $C_6$–$C_{10}$ aryl group, a $C_5$–$C_8$ saturated cyclic group, or a 4–10 membered heterocyclic group; and said alkyl, alkenyl, cycloalkyl, aryl and heterocyclic groups are optionally substituted by 1 to 3 substituents independently selected from halo, cyano, nitro, trifluoromethyl, trifluoromethoxy, azido, —$NR^{13}SO_2R^{15}$, —$SO_2NR^{12}R^{13}$, —$C(O)R^{12}$, —$C(O)OR^{12}$, —$OC(O)R^{12}$, —$NR^{13}C(O)OR^{15}$, —$NR^{13}C(O)R^{12}$, —$C(O)NR^{12}R^{13}$, —$NR^{12}R^{13}$, —$OR^{12}$, $C_1$–$C_{10}$ alkyl, $C_2$–$C_{10}$ alkynyl, —$(CR^{13}R^{14})_t(C_6$–$C_{10}$ aryl), and —$(CR^{13}R^{14})_t$(4–10 membered heterocyclic);

Z is an aromatic 4–10 membered heterocyclic group, substituted by 1 to 4 $R^6$ substituents;

each $R^{12}$ is independently selected from H, $C_1$–$C_{10}$ alkyl, —$(CR^{13}R^{14})_t(C_3$–$C_{10}$ cycloalkyl), —$(CR^{13}R^{14})_t(C_6$–$C_{10}$ aryl), and —$(CR^{13}R^{14})_t$(4–10 membered heterocyclic); said cycloalkyl, aryl and heterocyclic $R^{12}$ groups are optionally fused to a $C_6$–$C_{10}$ aryl group, a $C_5$–$C_8$ saturated cyclic group, or a 4–10 membered heterocyclic group; and the foregoing $R^{12}$ substituents, except H but including any optional fused rings, are optionally substituted by 1 to 3 substituents independently selected from halo, cyano, nitro, trifluoromethyl, trifluoromethoxy, azido, —$C(O)R^{13}$, —$C(O)OR^{13}$, —$OC(O)R^{13}$, —$NR^{13}C(O)R^{14}$, —$C(O)NR^{13}R^{14}$, —$NR^{13}R^{14}$, hydroxy, $C_1$–$C_6$ alkyl, and $C_1$–$C_6$ alkoxy;

each t is independently an integer from 0 to 5;

each $R^{13}$ and $R^{14}$ is independently H or $C_1$–$C_6$ alkyl, and where $R^{13}$ and $R^{14}$ are as —$(CR^{13}R^{14})_t$ each is independently defined for each iteration of t in excess of 1;

$R^{15}$ is selected from the substituents provided in the definition of $R^{12}$ except $R^{15}$ is not H;

$R^{16}$ is selected from the list of substituents provided in the definition of $R^{12}$ and —$SiR^{17}R^{18}R^{19}$; and, $R^{17}$, $R^{18}$ and $R^{19}$ are each independently selected from the substituents provided in the definition of $R^{12}$ except at least one of $R^{17}$, $R^{18}$ and $R^{19}$ is not H;

which method comprises reacting in an appropriate solvent in the presence of a suitable base a compound of the formula

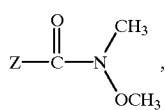

wherein Z is as defined above;
with a compound of the formula

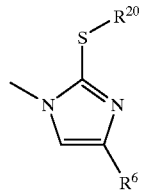

wherein $R^6$ is as defined above and $R^{20}$ is selected from H and phenyl;

thereby obtaining a compound of the formula

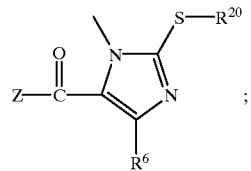

and removing from the compound of formula 31 so obtained the —$SR^{20}$ group, either:
a) reductively, with a nickel catalyst; or
b) oxidatively, with nitric acid or with aqueous hydrogen peroxide in acetic acid.

* * * * *